(12) United States Patent
Logothetidis et al.

(10) Patent No.: US 10,420,732 B2
(45) Date of Patent: Sep. 24, 2019

(54) METHOD FOR PRODUCTION OF NANOPOROUS MULTI-LAYER BIODEGRADABLE POLYMERIC COATINGS AND PRODUCTS THEREOF

(71) Applicants: Greek Aristotle University of Thessaloniki-Research Committee, Salonika (GR); Stergios Logothetidis, Salonika (GR); Varvara Karagkiozaki, Salonika (GR)

(72) Inventors: Stergios Logothetidis, Salonika (GR); Varvara Karagkiozaki, Salonika (GR)

(73) Assignees: Aristotle University of Thessaloniki-Research Committee, Salonika (GR); Stergios Logothetidis, Salonika (GR); Varvara Karaskiozaki, Salonika (GR)

( * ) Notice: Subject to any disclaimer, the term of this patent is extended or adjusted under 35 U.S.C. 154(b) by 0 days.

(21) Appl. No.: 14/015,530

(22) Filed: Aug. 30, 2013

(65) Prior Publication Data
US 2014/0072608 A1 Mar. 13, 2014

(30) Foreign Application Priority Data
Aug. 30, 2012 (GR) .................................. 120100450

(51) Int. Cl.
| | |
|---|---|
| *A61K 9/70* | (2006.01) |
| *A61L 27/34* | (2006.01) |
| *A61L 27/54* | (2006.01) |
| *A61L 27/56* | (2006.01) |
| *A61L 27/58* | (2006.01) |
| *A61L 29/08* | (2006.01) |
| *A61L 29/14* | (2006.01) |
| *A61L 29/16* | (2006.01) |
| *A61L 31/10* | (2006.01) |
| *A61L 31/14* | (2006.01) |
| *A61L 31/16* | (2006.01) |

(52) U.S. Cl.
CPC ............ *A61K 9/7007* (2013.01); *A61L 27/34* (2013.01); *A61L 27/54* (2013.01); *A61L 27/56* (2013.01); *A61L 27/58* (2013.01); *A61L 29/085* (2013.01); *A61L 29/146* (2013.01); *A61L 29/148* (2013.01); *A61L 29/16* (2013.01); *A61L 31/10* (2013.01); *A61L 31/146* (2013.01); *A61L 31/148* (2013.01); *A61L 31/16* (2013.01); *A61L 2400/12* (2013.01); *A61L 2420/02* (2013.01); *A61L 2420/06* (2013.01); *A61L 2420/08* (2013.01)

(58) Field of Classification Search
CPC ............ A61L 2420/02; A61L 2420/06; A61L 2420/08; A61L 27/56; A61L 29/146; A61L 31/146; A61K 9/7007
See application file for complete search history.

(56) References Cited

U.S. PATENT DOCUMENTS

| | | | | |
|---|---|---|---|---|
| 6,458,069 | B1 * | 10/2002 | Tam ..................... | A61K 9/1641 600/3 |
| 2014/0170204 | A1 * | 6/2014 | Desai ................... | A61F 9/0017 424/443 |

OTHER PUBLICATIONS

Osilla (http://www.ossila.com/pages/spin-coating) accessed Jun. 22, 2015.*
Karagkiozaki, V. et al. "Development of a nanoporous and multilayer drug-delivery platform for medical implants" International Journal of Nanomedicine 2012:7 5327-5338 (Year: 2012).*
Osilla (http://www.ossila.com/pages/spin-coating) accessed Jun. 22, 2015. (Year: 2015).*

* cited by examiner

*Primary Examiner* — Andrew S Rosenthal
(74) *Attorney, Agent, or Firm* — James Creighton Wray

(57) ABSTRACT

The present invention relates to the design and development of a drug delivery nanoplatform that consists of nanoporous, multi-layer biodegradable polymeric (BP) thin films for controlled release of its payload. The method is used notably to synthesize nanoporous BP coatings as drug delivery vehicles exhibiting uniform nanopores with tailored characteristics for control of drug delivery and release. It enables the multiplex delivery of drugs that can be eluted at desirable time intervals in line with each medical need. Atomic Force Microscopy and Spectroscopic Ellipsometry are applied for determining nanoporosity, thickness, drug loading, structural properties, and quality of the BP films ensuring the quality control of the final product. The complete degradation of the polymers minimizes the toxicity within the human body and such nanoplatform can be used in a wide range of drug eluting and other medical implants and biomedical devices.

13 Claims, 11 Drawing Sheets

METHOD FOR PRODUCTION OF NANOPOROUS MULTI-LAYER BIODEGRADABLE POLYMERIC COATINGS AND PRODUCTS THEREOF

TECHNICAL FIELD

The present invention relates to a method for design and development of nanoporous, biodegradable polymeric thin films in a single or multi-layer configuration with tailored properties notably for controlled drug delivery and release to be applied for implants and biomedical devices.

TECHNOLOGICAL BACKGROUND

In medical implants industry, there is a strong necessity for the development of nanoporous, biodegradable polymeric thin films to serve as drug eluting nanosystems and tailoring of their properties for controlled drug delivery and release. The existing technology for drug eluting implants enables mostly either the development of polymeric matrices loaded with drugs or the formation of pores or reservoirs with micrometer dimensions onto the implant surfaces [1-3]. Hence, such microporosity hinders the sustained and controlled release of the drug at the diseased site which is essential for the optimal rate and dose regimen.

Especially, in the case of drug eluting stents (DES), the medical device comprises a basecoat polymeric matrix loaded with anti-proliferative drugs deposited onto stent surface and a top coat to serve as diffusion barrier for drug release [4]. A wide range of biomaterials both bioabsorbable and biostable ones have been reported as drug eluting coatings that have encapsulated the therapeutic agents/drugs by applying, though not limited, the dipping, spraying, spincoating technologies [4, 5].

Up to date, diverse drugs for local delivery from DES surface have been reported, including anti-proliferative agents, such as rapamycin, paclitaxel, everolimus, zotarolimus, colchicine, ACE inhibitors, anti-inflammatory drugs and anti-oxidants,—such as corticosteroids, statins, probucol—, anti-platelet and anti-coagulant drugs,—such as corticosteroids heparin and heparin fragments, hirudin, aspirin, dypiridamole, platelet GP IIb/IIIa receptor antagonists, ticlopidine, clopidogrel—and genes. However, late thrombosis, inflammation, hypersensitivity reactions and endothelium healing delay are of major concern [6-8].

Indeed, it has been shown that the excessive burst release of drugs from implant surface and non-biodegradable polymer coatings employed by DES impair stent strut endothelialisation and may induce late stent thrombosis.

PRIOR ART

Document EP 1 557 183 discloses a device comprising multilayer coating and comprising polymeric materials deposited by a method of peripheral coating. These materials can include any pharmaceutical. Said document neither addresses nor discloses nanopores however.

AIM OF THE INVENTION

The objective technical problem to be solved is thus stated as providing a coating process that allows a rapid release of pharmaceutical substance from the outermost layers and prolonged drug release from the innermost layer.

This invention actually lies on the design and fabrication of nanoporous, biodegradable, polymeric nanocoatings in a multi or single layer—such as blends—configuration that constitute a drug eluting nanoplatform for medical implants and biomedical devices to overcome the shortcomings in the prior art. This nanoplatform may be applied to the delivery of drugs, therapeutic agents, nanomedicines, or/and compounds, without being limited thereto.

A purpose of the invention is the synthesis of nanoporous materials (laminates, polymeric) to release drug in a controlled manner from the surface of the implant due to the existence of nanopores and selecting polymer materials with different degrees of degradation that will make up the outer and inner layers.

SUMMARY OF THE INVENTION

Controlled drug delivery and release is feasible by means of the thorough tailoring of the structural properties and nanoporosity of the thin films in line with the design of the nanoplatform and the diversity of nanopores that may serve as drug reservoirs with multiplex loading capacities.

There is thus proposed according to a main embodiment of the invention a method for the fabrication of biodegradable polymeric thin films which is featured by nanopores with tailored characteristics in multi-layers or single layer blends, forming a delivery nanoplatform wherein it is specified to achieve a controlled and steady release of its payload, such as drug, and the preparation steps are carried out in the following specified order:

(a) Selection of biodegradable polymers hereinafter referred to as BP based on their degradation rates, monomers ratio, molecular weight, concentration and polymer blend ratio;

(b) 'Spin coating' of the selected polymers onto cleaned inorganic or organic substrates;

(c) The BP solution should be spin coated and then left overnight to slow dry, wherein the increase in the spinning speed leads to an increase in the pore diameter and a decrease in the pore density and the decrease in the polymer concentration keeping constant the rotation speed and spinning time, results in an increase in pore diameter, pore density of the engineered thin films;

(d) Preparation of organic solution containing of the active drug and BP at different ratios, well dissolved in organic solvent, in respect to the desirable drug concentration for each medical need;

(e) 'Spin coating' of the solution derived from step (d) onto the said biodegradable polymeric layers and sterilization, and (f) Determining nanopores characteristics, thickness, concentration and release, optical properties, and quality of said biodegradable polymeric thin films ensuring the quality control of the drug loaded materials and independently of the complexity of the nanoplatform.

So nanoporous coatings, nanocoatings, thin films, drug delivery nanosystems, drug delivery nanoplatform are thus proposed wherein a method for design and development of a nanoplatform is presented for the delivery and controlled release of one or more drugs, therapeutic agents, nanomedicines, or/and compounds for medical implants and biomedical devices that it is composed of nanoporous, multi- or single layers of biodegradable polymeric BP thin films featured by nanopores with tailored properties.

Nanotechnology enables the development of nanomaterials that can be used as drug delivery vehicles to deliver their payloads at the diseased sites. It offers nanotools to monitor biological interactions at atomic level and it deals with the optimization of implant surface, by the design and development of biocompatible nanocoatings that minimize implants' failure [9]. Nanocoatings hold promise to solve several problems present in conventional implant coatings.

Nanoporous coatings with pore sizes less than 100 nm are considered to exhibit superior drug eluting capacities as porosity of such low dimensions contributes to the material's high active surface and drug loading [10]. Their nanostructured surface resembles the extracellular matrix of native tissues enhancing tissue regeneration and the implant's integration to the surrounding tissues.

There are a few fabrication methods and materials for the development of drug delivery nanocarriers [11-12]. To date, numerous bottom-up and top-down nanofabrication technologies, though not limited to, involving electrospinning, phase separation, thin film deposition, chemical and physical vapor deposition, sputtering, self-assembly processes, sol gel, chemical etching, nano-imprinting, photolithography, are available to synthesize nanomaterials with ordered or random nanotopographies [13]. Hence, the use of inorganic—metals and their alloys—and non-biodegradable polymers—such as block copolymers—may cause the complications of inflammation and thrombosis due their permanent presence in the human body [14, 15]. Moreover, there is a lack of fabrication methods for development of nanoporous biodegradable polymeric thin films/nanocoatings in a multilayer or single structure to be applied into implants and medical devices for the delivery and release of therapeutic agents, drugs and compounds in a controllable manner. Even more, the lack of monitoring and control of the drug delivery systems leads to unfavourable drug release profile. This is very important since that defines the quality of the final drug eluting implant and its effectiveness to treat the targeted disease. It thus appears advantageous to design and develop a drug delivery nanoplatform for implantable or biomedical devices that comprises of nanoporous thin films—in nm dimensions—with tailored properties for the precise control of the release of the therapeutic agents. It also appears to be advantageous to design and develop drug delivery nanosystems for implantable devices that can elicit one or more different drugs, therapeutic agents, nanomedicines, or/and compounds at different time intervals for short-term and more prolonged, sustained therapeutic effect in relation to each medical need.

The formation of nanopores is attributed to the spinodal decomposition mechanism [20]. The morphology evolution is strongly dependent on the polymer blend ratio and the film thickness. If the weight content of one component in a polymer blend is much higher—about 90%— than the other component, then small holes are observed. When this fraction decreases to about 50%, the diameter of the holes increases and the holes starts to coalesce. In the case where the blend ratio of PCL:PLGA is 90:10, the presence of spherulites is evident, whereas in the ratio PCL:PLGA of 50:50 the holes between the spherulites coalesce. When the blend ratio of PCL:PLGA is 10:90, highly nanoporous thin films can be synthesized. When the blend ratio of PCL:PLGA ranges from 25:75 up to 5:95, highly nanoporous thin films can be synthesized by spin coating due to the spinodal decomposition mechanism.

This spinodal decomposition mechanism enables the manufacturing of nanoporous thin films made of BP blends by other wetting, printing and deposition techniques, such as spraying, dipping, gravure printing.

An example of printing a nanoporous blend polymer layer for drug delivery is presented significantly, in addition to spin coating technique.

The uniformity of the nanopores on the BP layer is apparent, wherein variations in the nanopore dimensions enable multiple drug delivery capabilities.

In overall, the performance of the drug eluting nanoplatform made from biodegradable polymers can be tuned by tailoring the molecular weight, crystallinity, surface free energy, hydrophilicity of the polymers and polymer blend ratio. However, additional factors are of equal importance: these include processing and manufacturing parameters, device design, and the site of implantation.

The nanoporosity, thickness and biodegradation rate of the BP nanolayers controls the drug release kinetics from the nanoplatform. By alterations in deposition parameters such as the polymer: drug ratio, polymer concentration, drug concentration, drug position etc desirable drug release profiles for short-term, medium-term and long-term use can be accomplished to meet the demands for various medical implants.

Deposition parameters control nanoporosity. Indeed, the AFM images demonstrated that by varying the spinning speed and the polymer concentration, multi sized and controllable nanopores can be produced. The increase in the spinning speed leads to an increase in the pore diameter, surface roughness and a decrease in the pore density. The decrease in the polymer concentration of the outer layer of PLGA2 keeping constant the rotation speed and spinning time, results in an increase in pore diameter, pore density and surface roughness of the biomaterials. Thus, the spin coating technique allows the manufacturing of controlled nanoporous BP thin films with reproducible results in the aspect of nanopores with tailored characteristics for optimized drug delivery and release.

The applications of the device body of the present invention yet comprise the following ones: biomedical tools, drug eluting medical devices and implants such as vascular and non vascular stent, drug eluting stent, guidewire, balloon cardiac catheter, cardiac pacemaker and implantable defibrillator, cardiac valve, surgical implant material, surgical tool, ocular and lens implant, orthopedic, spine and dental implants, food packaging, clothing, but it is not limited thereto.

According to a further embodiment of the method according to the invention, the determination of the nanopores characteristics, including surface nanotopography and roughness of the said polymeric thin films by AFM and of the thickness, drug concentration and distribution, optical properties, and quality of the films, is calculated by using Spectroscopic Ellipsometry.

According to a preferred embodiment of the method according to the invention, during said steps (a) and (e), the drug loaded biodegradable polymers are selected to be deposited in a way that the biodegradable polymers BP with slow degradation rate constitute the inner layer of the platform for a prolonged drug release, whereas the outer and intermediate drug loaded layers have quicker degradation rates for short and medium term drug release.

This distinguishes over above identified prior art EP 1 557 183 in that the polymer slow degradation constitutes the inner layer, whereas the outer and intermediate layer that is loaded with drug have faster degradation. The technical effect that can be recovered from this difference is the following. The outer layer having a faster rate of degradation relative to the inner layer allows a rapid and short release of a pharmaceutical substance, while the inner layer having a slow degradation rate will provide a sustained release of medicament.

Thanks to the invention, there is thus proposed the design of a drug delivery nanoplatform wherein the drug loaded BP nanolayers are selected to be deposited in a way that the BP thin film with slow degradation rate constitute the inner layer of the platform for a prolonged drug release whereas the outer and intermediate drug delivery nanolayers have quicker degradation rates for short and medium term drug release.

The nanoporosity, thickness, biodegradation rate of the BP nanolayers, type of drug, and drug position, controls the drug release kinetics from the nanoplatform. So, in the external BP nanolayer where the degradation rate is higher, therapeutic agents, drugs, peptides, growth factors, for short-term therapeutic activities can be delivered, wherein for medium-term and sustained therapeutic effects the appropriate agents or drugs should be delivered in the medium nanolayer. To achieve long-term therapeutic effects, the drugs, agents should be delivered in the internal BP nanolayer that exhibits slow degradation rates.

The multilayer structure of the drug delivery nanoplatform enables the loading of one or more different drugs into the different layers for multiplex drug activities at specific time intervals. A directional and controlled drug release from the nanoplatform can be achieved by tailoring the nanopores such as dimensions, interconnectivity and density, the thickness of the multi-layer thin films and by the different degradation rates of each layer.

A diversity of drugs can be encapsulated into the outer, intermediate or inner biodegradable layer and even different drugs can be incorporated into the different layers of the nanoplatform. This design of the nanoplatform enables the desirable time-dependant drug elution determined by the degradation process of each layer.

Thus, the spin coating technique enables the synthesis of the BP thin films characterized by high nanoporosity and uniformity of the nanopores essential for drug delivery. The pore distribution in the nanoporous biomaterials is a key factor for determination of drug release kinetics and its directional control. The tailoring of the nanopores features can be achieved by alteration in deposition parameters.

Nanoporosity is determined mainly by the structural properties of the BPs, polymer concentration and polymer blend ratio, the order of the successive deposition of the BP nanolayers and the biodegradation rate of the BPs.

In controlled polymeric drug delivery systems, the drug delivery rates are mainly determined by the dynamics of polymer degradation, which is strongly related to polymer structure, morphology and properties.

The results show that Spectroscopic Ellipsometry was successfully employed for the determination of the optical properties, thickness and structural characteristics of the spin coated triple polymeric thin films with or without drug.

In other words, to achieve the objectives above, the present invention employs the technical solutions as follows: the drug delivery nanoplatform used in drug eluting implants/biomedical devices of the present invention consists of multilayer biodegradable polymeric BP thin films—exhibiting nanoscale dimensions—or single layer BP blends, featured by tailored nanopores loaded with one or more active drugs, therapeutic agents, and/or compounds for their controlled and steady release.

The design of the drug delivery nanoplatform is based on the specific order of the BP layers in line with their degradation rates and the incorporation of the candidate therapeutic agents within the layers to meet the implant requirements for a specific medical application. Different active drugs, agents or/and compounds, can be delivered within the different BP nanoporous layers and can be eluted at specific time intervals for short-term, medium term and more prolonged release at the diseased site.

A diversity of biodegradable polymers, such as different types of Poly (DL-lactide-co-glycolide) (PLGA) in terms of lactide:glycolide ratio, polycaprolactone (PCL) etc with variations in degradation rates may constitute the nanoporous layers of the platform and they can be deposited by spin coating technique. In addition, other BPs, though not limited to BP aliphatic polyesters, notably homopolymers and copolymers of lactic acid, glycolic acid, trimethylene carbonate, and blends, can be used as well for the nanoplatform formation.

The drug delivery BP can be selected to be deposited in a way that the BP with slow degradation rate constitute the inner layer of the platform for a prolonged release of its payload whereas the outer and intermediate drug delivery nanoporous layers have quicker degradation rates for short and medium term drug release.

Besides spin coating, other wetting and printing techniques, including but not limited, to gravure and ink jet printing, dip coating, spray coating, can be also applied for the fabrication of the nanoporous BP layers onto organic and inorganic substrates. The monomers ratio, molecular weight, crystallinity, hydrophilicity and surface free energy of the BPs, the BPs deposition in a specific order, the polymer: blend ratio, the polymer: drug ratio in the thin films, combined with the desirable drug concentration, position within the layers and drug actions are the main parameters to consider for optimization of the fabrication process.

The full biodegradation of the said polymers minimizes inflammation, thrombosis and any toxicity that may occur after their implantation and permanent presence to human body.

The design of the platform and the selection of polymers and drugs should be made in line with the specific medical application.

Multi sized nanopores formed on the surface or in the bulk of the films can serve as drug reservoirs with multiplex capabilities. In the case of the said DES nanoplatform, a representative drug, dipyridamole (DPM) an antiplatelet drug known to inhibit clotting was encapsulated into the external and medium nanolayers of the polymeric nanoplatform and the release of the drug was monitored over time by drug release kinetics studies. Dexamethasone (DEX), a corticosteroid with anti-inflammatory properties has also been delivered into the external and mediate nanolayers and studies on drug release kinetics follow.

The pore distribution in the nanoporous biomaterials is a key factor for determination of drug release kinetics and its directional control. By varying the size—i.e. diameter, volume—and density of the nanoporous reservoirs, a range of therapeutic agent loading levels can be achieved.

The control of nanoporosity and thickness of the engineered nanomaterials can be achieved upon the fabrication method, e.g. alterations in deposition parameters, polymer types and ratios, in line with ultra sensitive measurements and monitoring by Atomic Force Microscopy (AFM) and Spectroscopic Ellipsometry (SE). The thorough characterization of the structural properties of the engineered systems is essential for the achievement of their functionality as well as for the prediction of their effectiveness.

By the SE, the determination of thickness, nanoporosity, optical, surface properties and quality of thin films and multilayer nanostructures enables the control of loading and release of pharmacologically active agents in order to achieve the site-specific action of the drug at the therapeutically optimal rate and dose regimen.

AFM is a very high-resolution type of scanning probe microscopy, with demonstrated resolution on the order of fractions of a nanometer. It can provide a detailful description of the nanotopography and nanopores characteristics notably including dimensions, shape, density and interconnectivity, of the BP thin films, essential for monitoring the drug delivery potential.

Methods for the fabrication and control in the production of nanoporous, BP thin films in multi-layers for drug eluting implants by wetting and printing techniques with priority to the properties of the surfaces and interfaces that are related to the functional properties of the intermediate and final products for controlled drug elution do not represent existing technologies.

By the described technology, the tailoring of the structural properties of the nanoporous multi layer nanoplatform leads to the improvement of its efficiency and performance for a wide spectrum of drug eluting implants and biomedical devices thereby including cardiovascular, orthopaedic, retinal, neurosurgical implants, intraocular lenses, surgical tools.

Therefore, an appropriate, fast and reliable development of a nanoplatform that consists of nanoporous and multi or single BP nanolayers combined with the monitoring and control process should: (a) control the technical requirements for the nanoporous materials and the nanoplatform architecture e.g. appropriate thicknesses, nanopore characteristics, efficient loading levels and therapeutic actions of drugs or compounds, polymer blend ratio, specific order of BP thin films with different degradation rates for time dependant release, etc, (b) tailor the drug loading capacities of the nanoplatform in order to achieve a controlled drug elution profile from implant/biomedical device surface, (c) monitor the surface properties and drug delivery within the nanolayers by a non-destructive and creditable methodology using AFM and SE.

According to another embodiment of the method according to the invention, the same manufacturing process is applied for the synthesis of nanoporous thin films made of blends of biodegradable polymers.

According to a still further embodiment of the method according to the invention, said thin films possess uniformly distributed nanopores with adjustable dimensions and density under different experimental conditions.

According to a specific embodiment, said steps of the abovementioned main embodiment of the method according to the invention are carried out in the specified order (a), (b), (c), (f) for the fabrication of drug-free nanoporous BP thin films as multi-layer or blends.

According to a yet further embodiment of the method according to the invention, the gravure printing technique is realized for the synthesis of nanoporous thin films made of blends of biodegradable polymers and the preparation steps consist of a) a selection of biodegradable polymers BP based on their degradation rates, monomers ratio, molecular weight, b) preparing the polymer blend by dissolving the said BPs at specific ratio in organic solvent, c) printing the polymeric mixture by the gravure printing technique under selected printing parameters and d) leaving the samples to slow dry for about 24 h.

According to an additional embodiment of the method according to the invention, the therapeutic agents that can be loaded into the present nanoporous platform include the following at least one substance: drugs, genes, peptides, nanomedicines, or/and compounds, but it is not limited thereto.

According to a further additional embodiment according to the invention, the method is remarkable by the development of a nanoporous platform with drug eluting capabilities as a final product consisting of either biodegradable polymeric thin films as multilayers or blends in order to be used for diverse medical implants and devices, such as vascular and non vascular stent, drug eluting stent, guidewire, balloon cardiac catheter, cardiac pacemaker and implantable defribilator, cardiac valve, surgical implant material, surgical tool, ocular and lens implant, orthopedic, spine and dental implants.

According to a main embodiment of the product according to the invention, biodegradable polymeric thin films produced according to a method as defined above are remarkable in that they possess nanopores with tailored characteristics as multi layers and blend single layers. This distinguishes over above identified prior art in that the polymer's slow degradation constitutes the inner layer whereas the outer and intermediate layer that is loaded with drug have faster degradation. The technical effect achievable from this difference is the following. The outer layer having a faster rate of degradation relative to the inner layer allows a rapid and short release of a pharmaceutical substance, while the inner layer having a slow degradation rate will provide a sustained release of medicament.

According to a particular embodiment of the product according to the invention, said biodegradable polymeric thin films are highly nanoporous, loaded with drugs, as multi layers to form a nanoporous platform for controlled drug delivery and release.

According to a more particular embodiment of the product according to the invention, said biodegradable polymeric thin films constitute a drug delivery nanoplatform for medical implants and biomedical devices, wherein the biodegradable polymers BP deposited in a way that the BP with a slow degradation rate constitute the inner layer of the platform for a prolonged drug release, whereas the outer and intermediate layers have quicker degradation rates for its short and medium term drug release.

In the following, a detailed description of a way of carrying out the invention, with the use of examples, explaining the application of the invention is presented, which is illustrated by appended drawings related to the invention.

A polymer concentration of 10 mg ml-1, spin-coated at 2000 rpm for 30 sec,

B polymer concentration of 10 mg ml-1, spin-coated at 3000 rpm for 30 sec and

C polymer concentration of 5 mg ml-1, spin-coated at 2000 rpm for 30 sec. The results were obtained through Atomic Force Microscopy and the scan size was 10 μm×10 μm. PLGA1 refers to PLGA 75:25, and PLGA2 to PLGA 65:35.

Figure 6:
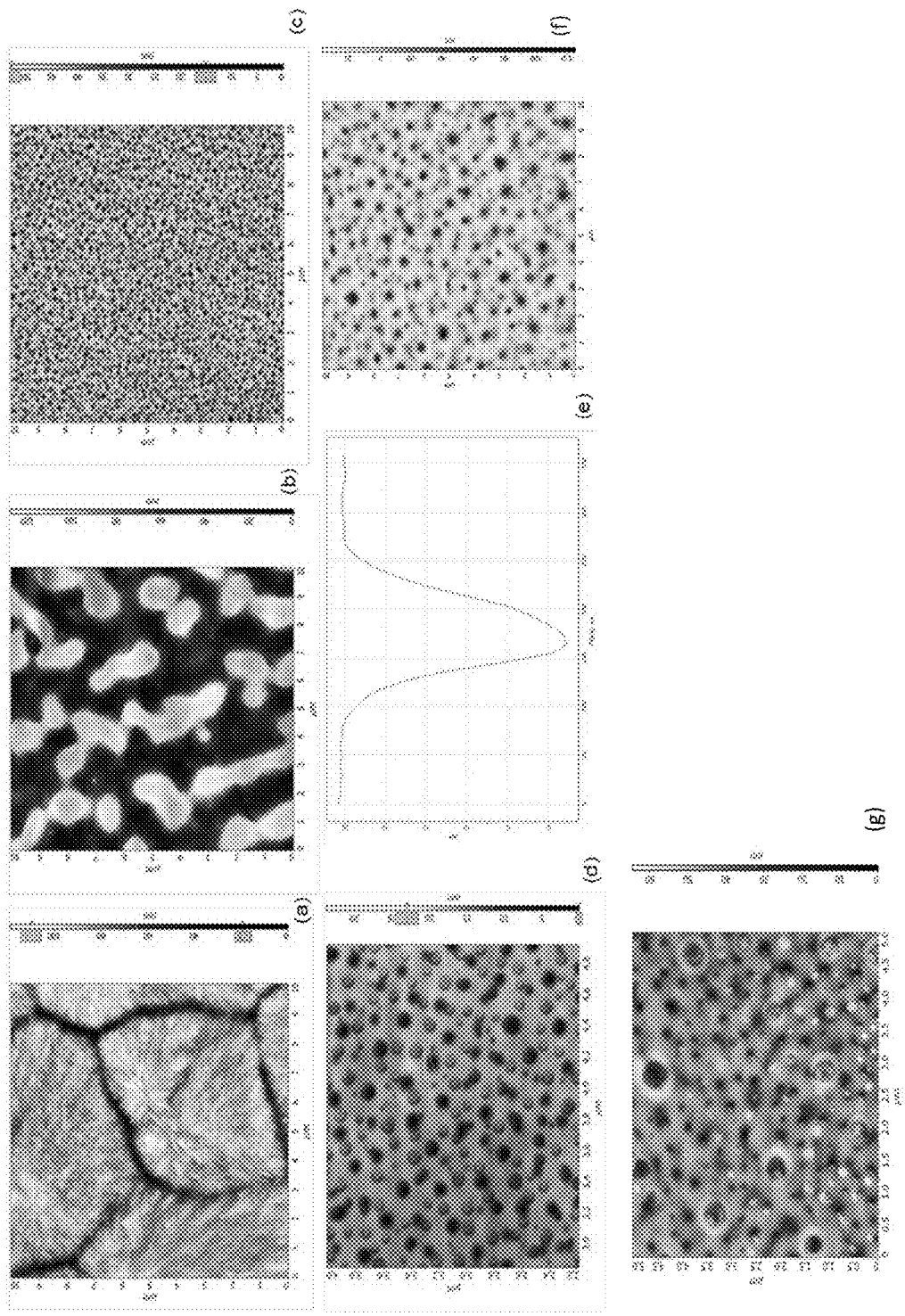

FIG. 6 shows topography images of the blend single nanolayer PLGA-PCL fabricated by spin coating under variable PCL:PLGA ratios.

(A) PCL:PLGA (90:10), (B) PCL:PLGA (50:50), (C) PCL:PLGA (10:90), spin-coated at 2000 rpm for 30 sec. The results were obtained through Atomic Force Microscopy and the scan size was 10 μm×10 μm, (D) PCL:PLGA (10:90) fabricated by gravure printing method with printing speed 10 m/min, (E) corresponding arbitrary-cross-section reveals the dimensions of the nanopores formed in the thin films, and (F) PCL:PLGA (20:80), spin-coated at 2000 rpm for 30 sec. (G) PCL:PLGA (10:90) thin film for delivery of dexamethasone (DEX), at polymer blend:DEX ratio 3:1.

The results were obtained through Atomic Force Microscopy.

Figure 7:
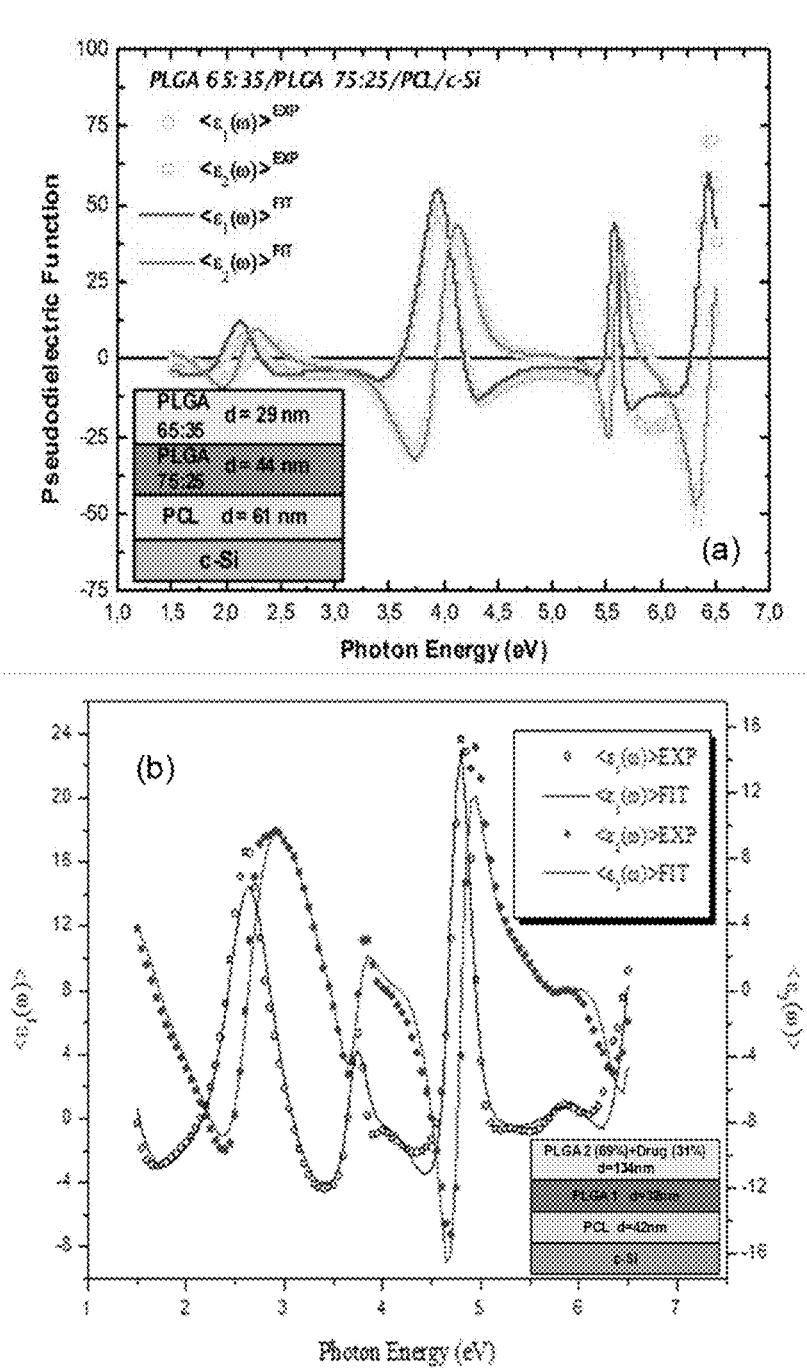

FIG. 7 represents the experimental pseudodielectric functions (symbols) of the triple layer PLGA2/PLGA1/PCL/c-Si (a), and the triple layer PLGA2 with drug/PLGA1/PCL/c-Si (b), wherein the solid lines corresponds the simulated ones determined by the use of best-fit results and PLGA2 denotes PLGA 65:35 and PLGA1 denotes PLGA 75:25.

Figure 8:
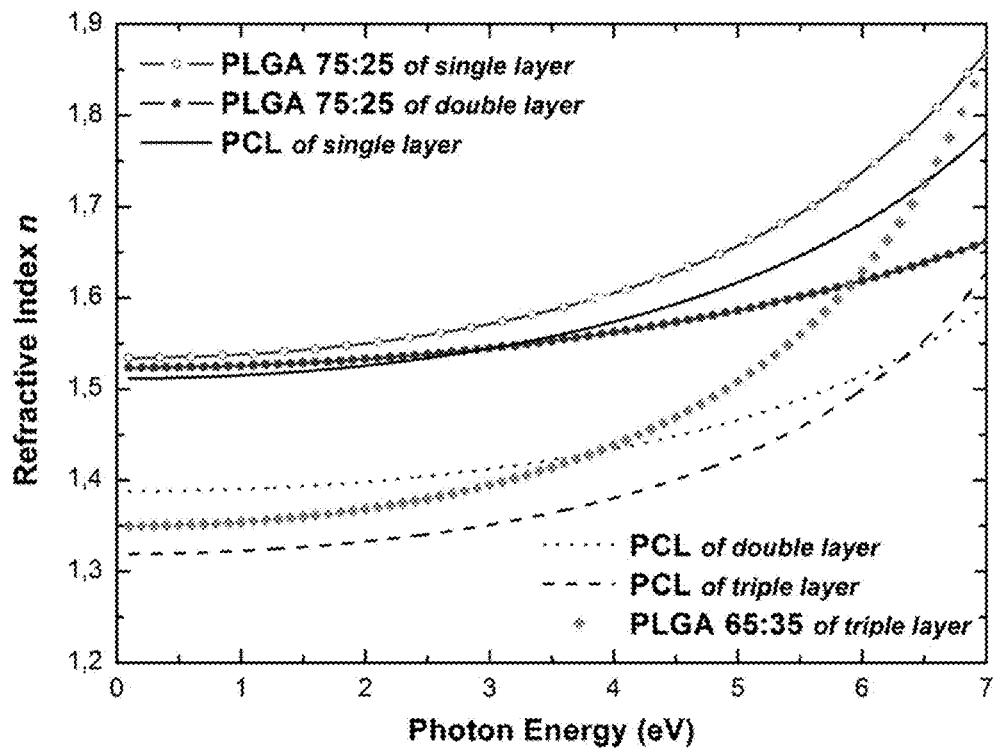

FIG. 8 shows the real part of the bulk complex refractive index n calculated using of best-fit parameters of the SE data analysis for the single layer polymeric films PLGA 1 (PLGA 75:25) and PCL, the PLGA 1 (PLGA 75:25) and PCL from the dual layer film, and the PLGA2 (PLGA 65:35) and PCL from the triple layer film. The results were obtained through the analysis of the measured SE spectra.

Figure 9A:
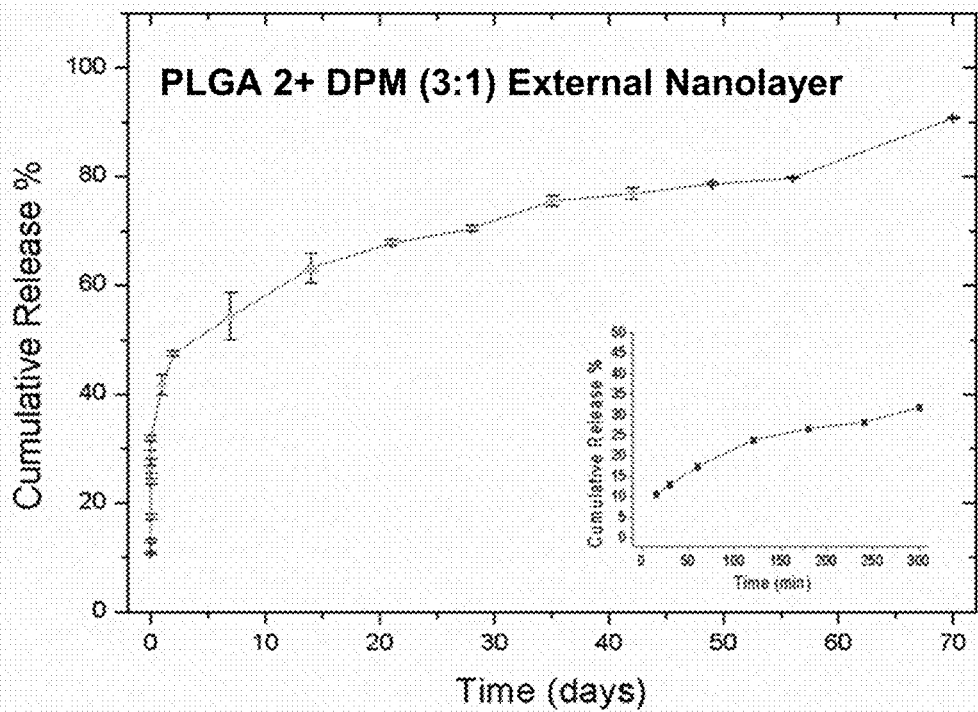
Figure 9B:
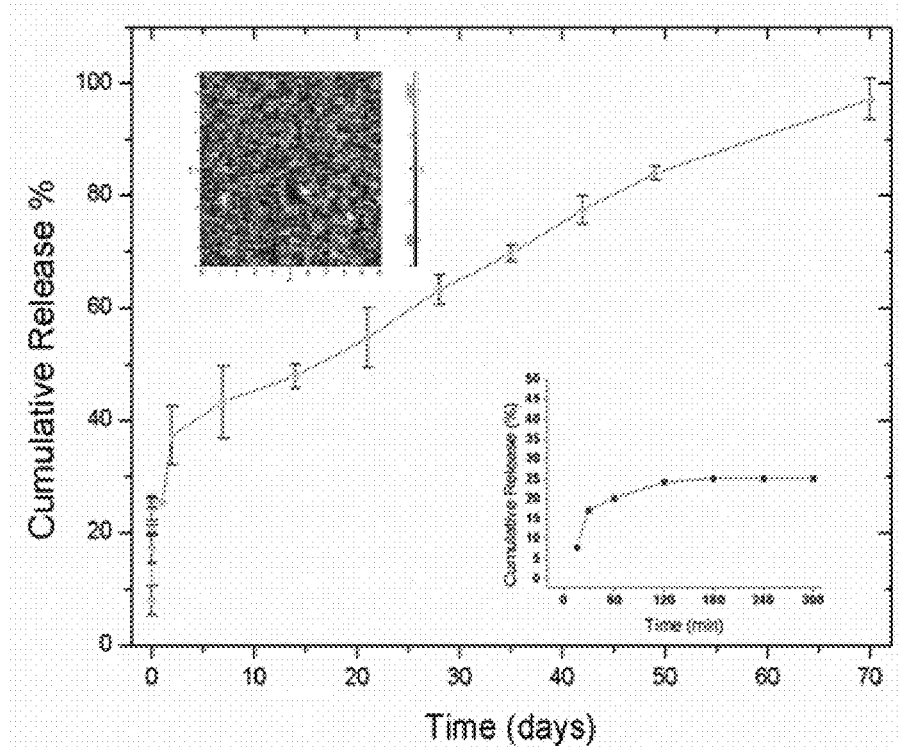
Figure 9C:
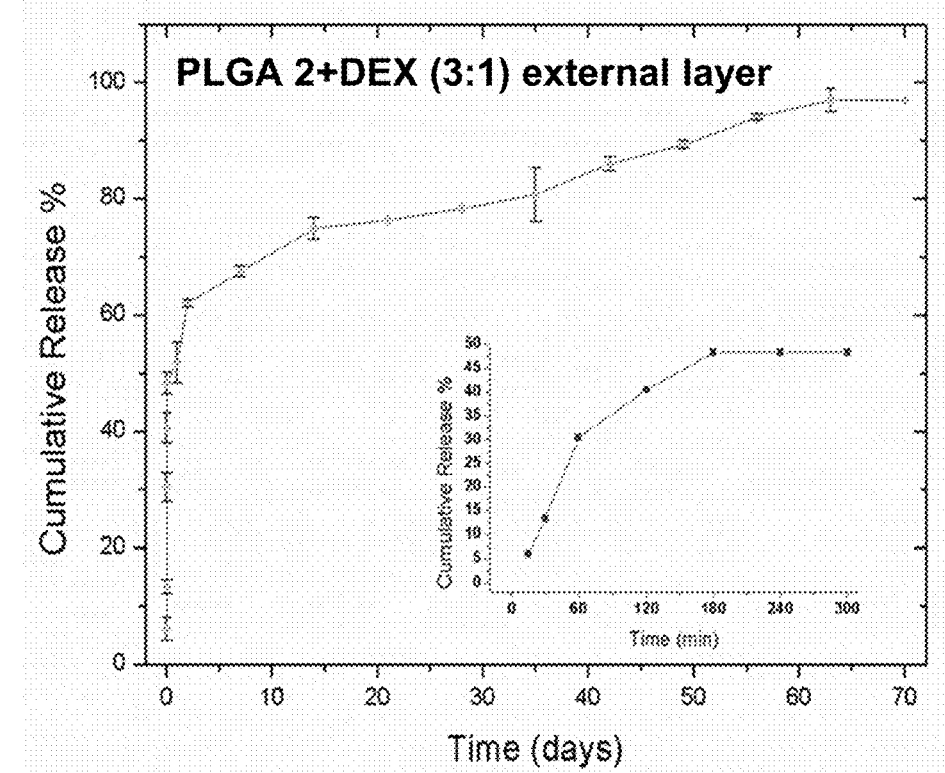

FIG. 9a shows the dipyridamole (DPM) cumulative release profiles from the outer layer PLGA2 of the multi-layer nanoplatform [PLGA2-PLGA1-PCL] with PLGA2: DPM 3:1 ratio wherein the inset graph depicts the burst effect that occurs during the first 5 hours. FIG. 9b shows the DPM cumulative release profiles from the PLGA2 of the multi-layer nanoplatform having an hydrophilic Poly(vinyl alcohol) (PVA) BP 4th nanolayer to coat the nanoplatform to increase its hemocompatibility and to reduce the initial amount release of the drug. There is a PLGA2: DPM 3:1 ratio wherein the inset image presents the AFM topography of the nanoporous platform that comprises of [PVA-PLGA2 with DPM-PLGA1-PCL], and the inset graph depicts the burst effect that occurs during the first 5 hours. FIG. 9c shows the dexamethasone (DEX) cumulative release profiles from the outer layer PLGA2 of the multi-layer nanoplatform [PLGA2-PLGA1-PCL] with PLGA2: DEX 3:1 ratio wherein the inset graph depicts the burst effect that occurs during the first 5 hours. Herein, PLGA2 denotes PLGA 65:35 and PLGA1 denotes PLGA 75:25.

Figure 10:
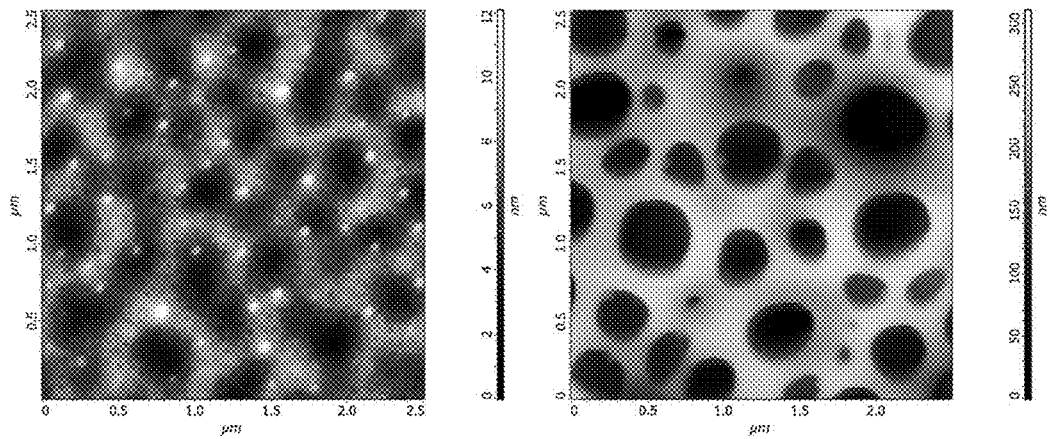

FIG. 10 shows the topography images of the triple nanolayer [PLGA2-PLGA1-PCL] loaded with DPM in the outer layer at PLGA:DPM 2:1 ratio as fabricated by spin-coating at 3000 rpm for 30 sec (left image), and after its degradation in PBS solution for 15 min (right image). The results were obtained through Atomic Force Microscopy and the scan size was 2.5 μm×2.5 μm, wherein PLGA1 refers to PLGA 75:25, and PLGA2 to PLGA 65:35.

Figure 11:
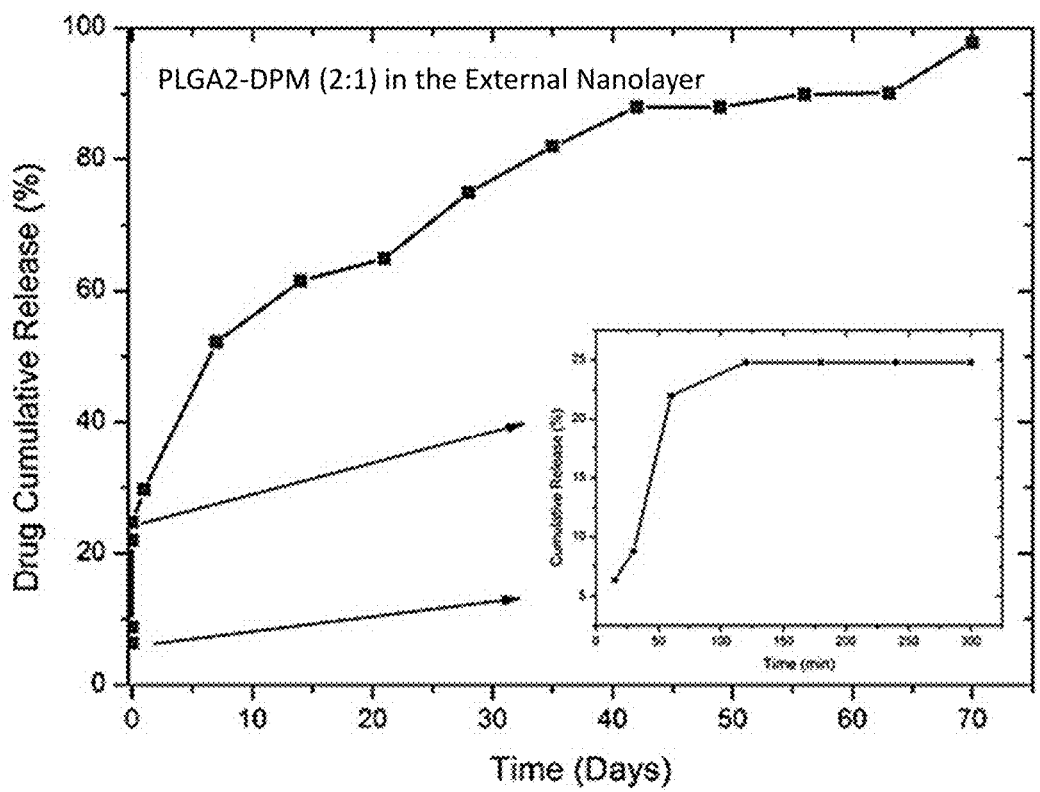

FIG. 11 shows the dipyridamole cumulative release profiles from the outer layer of the three layer sample [PLGA2-PLGA1-PCL] with PLGA2:DPM 2:1 ratio wherein the inset graph depicts the burst effect that occurs during the first 5 hours. The results were obtained through UV-visible spectrophotometer measurements of the free drug that absorbs at 292 nm. PLGA1 refers to PLGA 75:25, and PLGA2 to PLGA 65:35.

Figure 12A:
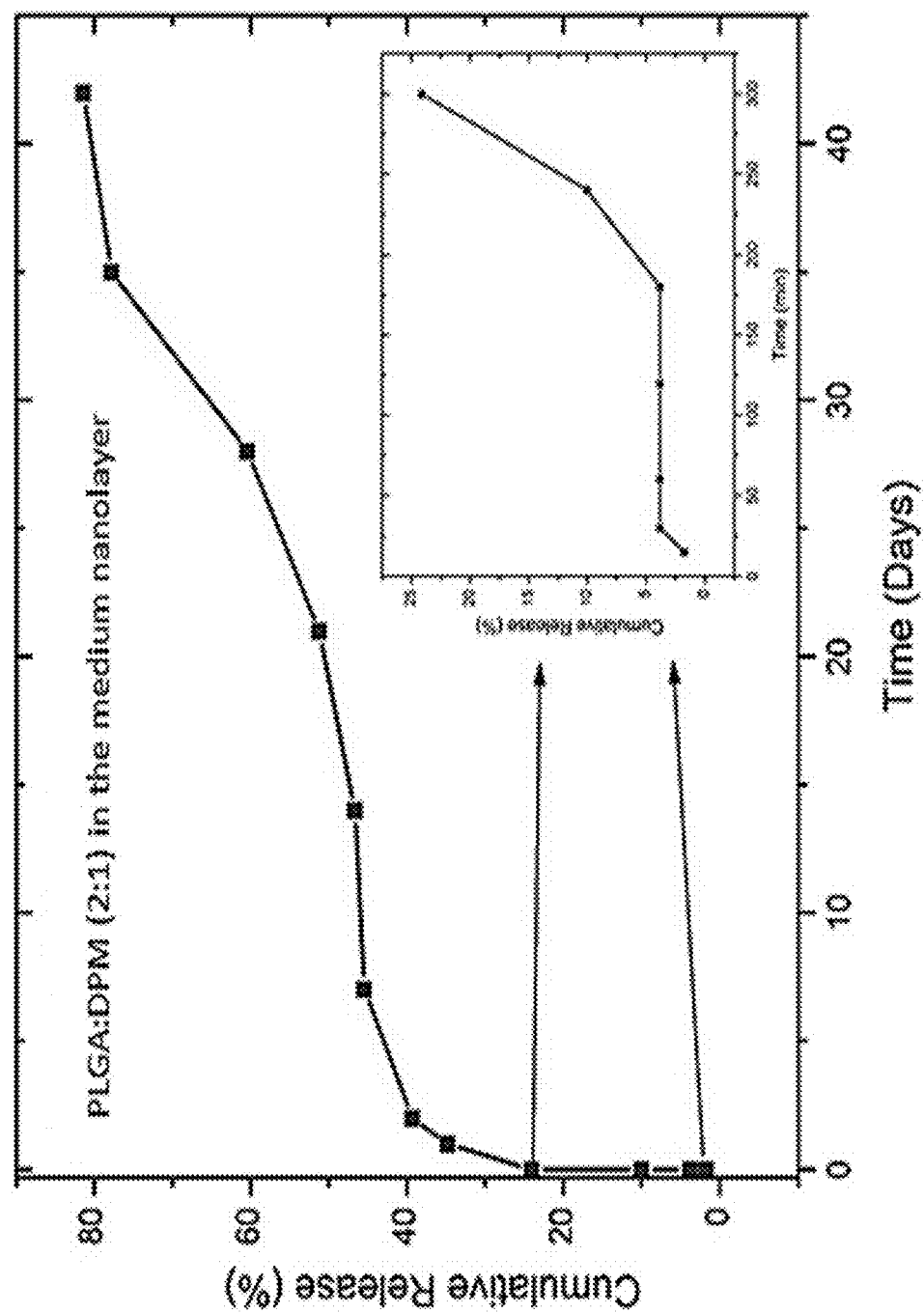
Figure 12B:
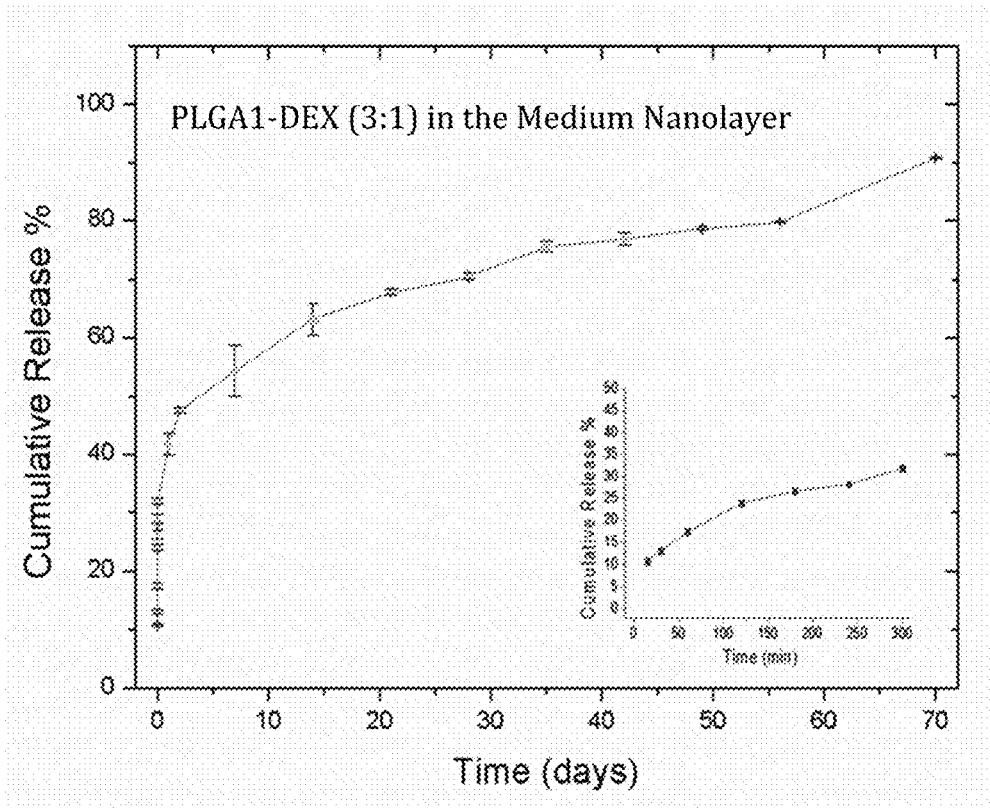
Figure 12C:
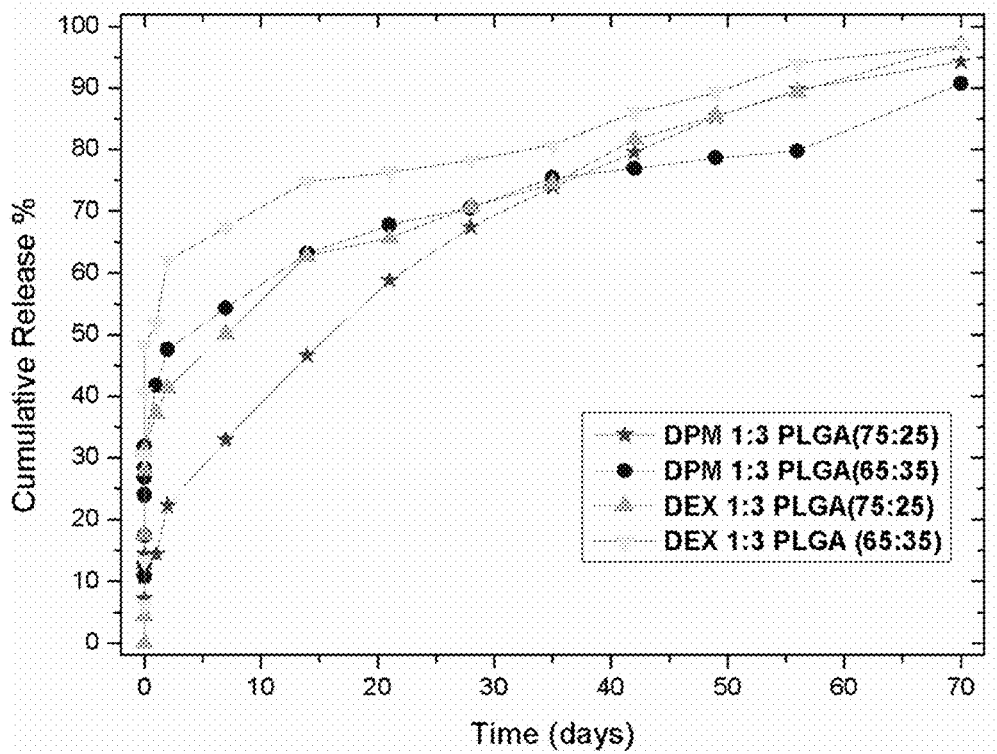

FIG. 12a shows the dipyridamole cumulative release profiles from the medium layer of the three nanolayer platform [PLGA2-PLGA1-PCL] with PLGA:DPM 2:1 ratio wherein the inset graph depicts the burst effect that occurs during the first 5 hours. FIG. 12b, shows the DEX cumulative release profiles from the medium layer PLGA2 of the multi-layer nanoplatform [PLGA2-PLGA1 with DEX-PCL] with PLGA2:DEX 3:1 ratio wherein the inset graph depicts the burst effect that occurs during the first 5 hours. FIG. 12c, shows the comparative diagram of the cumulative release profiles of the DPM and DEX drugs in relation to their position within the external or medium thin films of the three nanolayer platform [PLGA2-PLGA1-PCL] keeping constant the drug:polymer ratio to 3:1. PLGA1 refers to PLGA 75:25, and PLGA2 to PLGA 65:35.

DESCRIPTION

The invention relates to a method for design and development of a nanoplatform for the delivery and controlled release of one or more drugs, therapeutic agents, nanomedicines, or/and compounds for medical implants and biomedical devices that it is composed of nanoporous, multi- or single layers of biodegradable polymeric (BP) thin films, which is featured by nanopores with tailored properties for the case of the following examples.

A first example consists of a design of a drug delivery nanoplatform based on a specific order of the drug loaded BP nanoporous layers and position of one or more drug within the nanolayers; the degradation rates of the BP thin films; the nanoporosity characteristics; the monomers ratio and molecular weight, the crystallinity and surface free energy of the BPs; the polymer blend ratio; the drug actions;

the drug concentration and polymer: drug ratio in the thin films, to meet the requirements for a specific medical application.

A further example consists of a design of a drug delivery nanoplatform wherein the drug loaded BP nanolayers are selected to be deposited in a way that the BP thin film with slow degradation rate constitute the inner layer of the platform for a prolonged drug release whereas the outer and intermediate drug delivery nanolayers have quicker degradation rates for short and medium term drug release.

A still further example consists of a design of a drug delivery nanoplatform for cardiovascular stents to inhibit stent thrombosis by the steady release of anti-platelet drugs and to reduce inflammation by the elution of anti-inflammatory agents.

A yet further example consists of a synthesis of nanoporous thin films as single and multi layers of BPs, such as PLGA with different lactide:glycolide ratios, PCL etc, on inorganic and organic polymeric substrates by spin coating and printing techniques.

Another example consists of a development of highly nanoporous thin films that consist of BP blends on inorganic and organic polymeric substrates by spin coating and though not limited, by other coating and printing techniques, such as electrospinning, spraying, dipping, ink-jet printing, gravure printing and vacuum deposition techniques.

A still other example consists of manufacturing of drug loaded nanoporous thin films, made of biodegradable polymers as single or multi-layers to form a drug delivery nanoplatform for implants and medical devices by applying spin coating and other wetting and printing techniques.

A yet other example consists of tailoring the surface properties, the nanopores characteristics, nanopores depth, diameter, density, thickness of the BP thin films for controlled drug delivery and release by alteration in deposition parameters in line with the derived spectroscopic ellipsometry and AFM data for thin films characterization and evaluation.

This method can be generally applied, notably in the case of monolayer and multilayer thin films of organic polymeric, biodegradable or not, nanomaterials that can be used for the production of nanoporous delivery systems for medical implants and devices. The nanoporous thin films can be used as nanocoatings for a wide spectrum of medical implants or biomedical devices, e.g. cardiovascular, orthopaedic, neuro implants, intraocular lenses, surgical tools, etc., to deliver and release drugs, therapeutic agents, nanomedicines, genes, peptides and compounds or to mimic the nanostructure texture of tissues for better integration of the implants in the surrounding tissues,—either loaded or non-loaded—nanoporous thin films, in accordance to each medical need.

In the case of drug delivery nanoplatform, the nanoporosity of the materials and surface properties are highly tailored to achieve controlled drug delivery and steady drug release. The biodegradability and good biocompatibility of the polymeric nanomaterials e.g. PLGA, PCL etc., minimize their toxicity after entrance into human body.

This drug delivery nanoplatform composed of nanoporous BP thin films, can be developed by spin coating, and though not limited, by other coating and printing techniques such as, electrospinning, spraying, dipping, ink-jet printing, gravure printing and vacuum deposition techniques. Moreover, it can be applied for all polymeric substrates such as Poly(Ethylene Terephthalate) (PET), Poly(Ethylene Naphthalate) (PEN), collagen, chitosan, etc and other flexible substrates as well as inorganic ones like stainless steel, silicon, titanium and other metals, glass etc.

Furthermore, it can be applied for all kinds of surface, and it can be used, though not limited, for the delivery of hydrophilic or lipophilic drugs, therapeutic agents and compounds, nanomedicines, genes, growth factors, peptides, to meet the requirements for each medical implant. The multilayer structure of the drug delivery nanoplatform enables the loading of one or more different drugs into the different layers for multiplex drug activities at specific time intervals.

A directional and controlled drug release from the nanoplatform can be achieved by tailoring the nanopores such as dimensions, interconnectivity and density, thickness of the multi-layer thin films and by the different degradation rates of each layer.

The realization of measurements by AFM and SE measurements in the spectral region of Vis-FUV is appropriate for the detailed characterization of the nanoporous materials, the nanoplatform architecture and drug encapsulation within the layers for tailored drug loading capabilities. By monitoring the nanopores characteristics, drug distribution and thickness of the layers, suitable modifications in deposition parameters can lead to desirable drug loading of the nanomaterials.

The measurements realized for the presentation and the use of the proposed technique is set out below.

In controlled polymeric drug delivery systems, the drug delivery rates are mainly determined by the dynamics of polymer degradation, which is strongly related to polymer structure, morphology and properties.

Figure 1A:
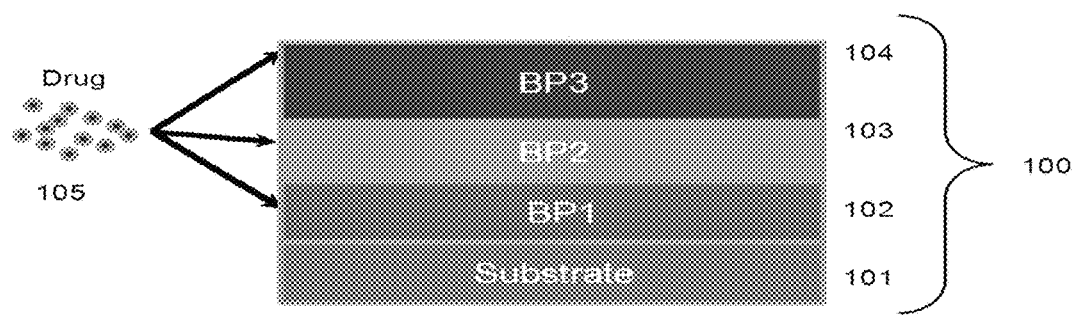
FIG. 1a is a schematic representation of the multilayered structure of the biodegradable polymeric nano-layers BP1, BP2, BP3 for the formation of the drug eluting nanoplatform for medical implants and biomedical devices.

FIG. 1a shows a schematic representation of the multilayered structure 100 of the biodegradable polymeric BP thin films 102, 103, 104 for the formation of the drug eluting nanoplatform for implants and devices. The design of the biodegradable nanoplatform is based on the requirements of each medical implant that it is aimed for coating its surface. Different classes of biodegradable polymers, e.g. BP1, BP2, BP3, etc, in terms of molecular weight, monomers ratio, crystallinity, hydrophilicity, surface free energy and especially of degradation rates can be deposited in a multi-layer structure onto inorganic or organic substrates 101 by applying spin coating technique to provide a controlled drug release.

Figure 1B:
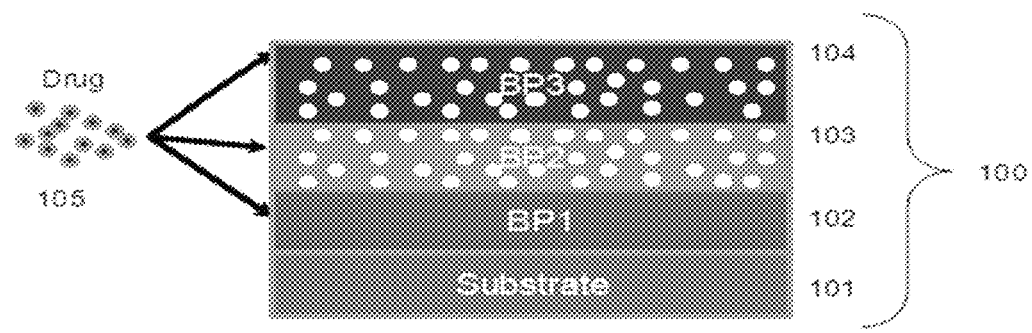
FIG. 1b is a schematic representation of the nanoporous multilayered structure of the biodegradable polymeric thin films BP1, BP2, BP3 that constitute the drug eluting nanoplatform for a controlled delivery and release of drugs, therapeutic agents, nanomedicines, and/or compounds.

FIG. 1b depicts a schematic representation of the nanoporous multilayered structure 100 of BP the biodegradable polymeric (BP) thin films 102, 103 for the formation of the drug eluting nanoplatform for implants and devices, that allows the controlled release of their therapeutic payloads through the nanopores.

A diversity of drugs can be encapsulated into the outer, intermediate or inner biodegradable layer 105 and even different drugs can be incorporated into the different layers of the nanoplatform. This design of the nanoplatform enables the desirable time-dependant drug elution determined by the degradation process of each layer.

Figure 2A:
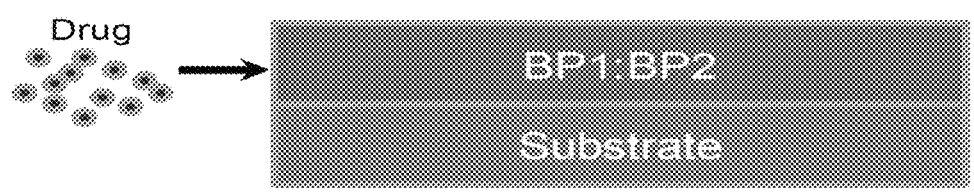
FIG. 2a is a schematic representation of the blend single layered structure of the biodegradable polymeric thin films BP1:BP2 for the formation of the drug eluting nanoplatform to be used as drug delivery nanosystem for medical implants and biomedical devices.
Figure 2B:
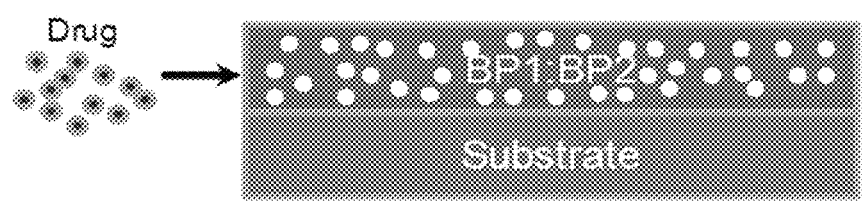
FIG. 2b is a schematic representation of the nanoporous blend structure of the biodegradable polymeric thin films (BP1:BP2) to be used as drug delivery nanosystems for medical implants and biomedical devices.

FIG. 2a shows a schematic representation of the blend structure—as a single nanolayer—of the biodegradable polymers BP1, BP2 for the formation of the drug eluting nanoplatform, wherein drugs or therapeutic agents can be delivered. FIG. 2b shows a schematic representation of a nanoporous BP blend in a single nanolayer structure by having a specific polymer blend ratio BP1:BP2, leading to controlled drug delivery and release. The appropriate blend of the biodegradable polymers can be spin coated onto inorganic or organic substrates for nanopores formation. Other wetting and printing techniques can be also applied involving, but not limited to spraying, dipping, ink-jet and gravure printing and other, to synthesize nanoporous thin films made of polymeric blends for drug loading activities from implant/device surface. A paradigm of such medical application is their deposition onto intraocular lenses placed after cataract surgery to release anti-inflammatory agents for reduction of complications.

Figure 3A:
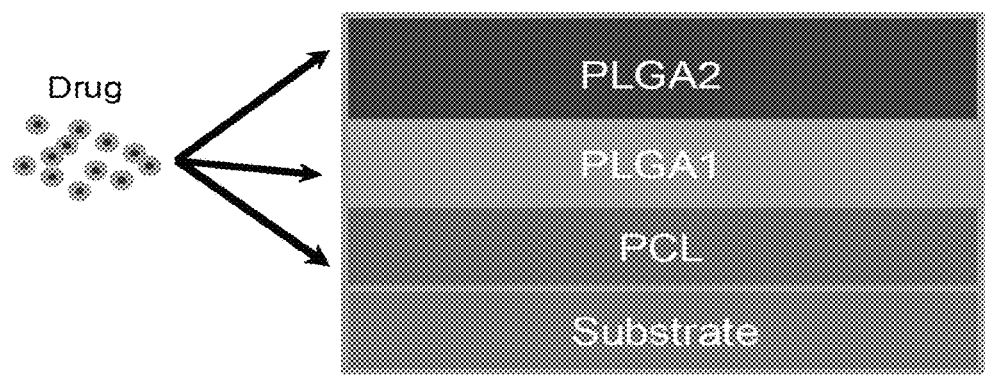
FIG. 3a is a schematic representation of the multilayered structure of the PCL, PLGA1, PLGA2 biodegradable polymeric nanolayers that can be loaded with drugs, therapeutic agents, nanomedicines, compounds to constitute the drug eluting nanoplatform for cardiovascular, intraocular lenses and other medical implants, biomedical devices. PLGA2 is referring to PLGA with faster degradation rate as compared to PLGA1 whereas PCL has the slower degradation rate.
Figure 3B:
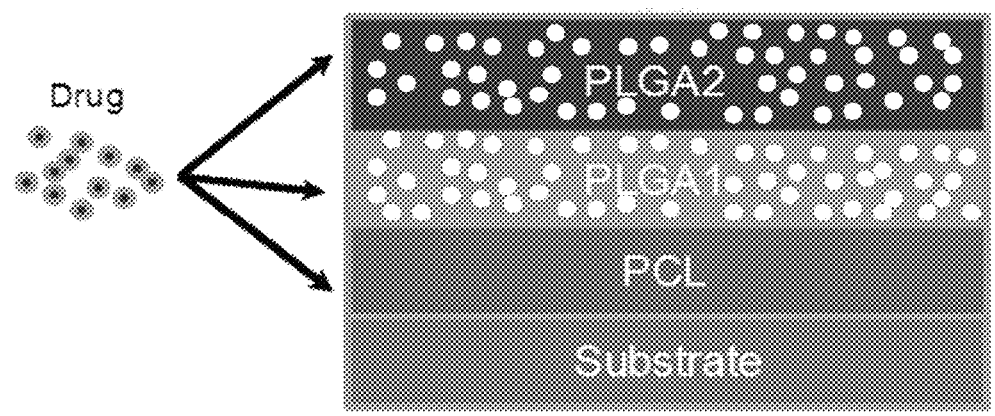
FIG. 3b is a schematic representation of the nanoporous multilayered structure of the PCL, PLGA1, PLGA2 nanolayers that constitute the drug eluting nanoplatform for controlled and sustained delivery and release of their payloads from implant surface.

FIG. 3a shows an example of the design of a BP drug eluted nanoplatform targeted for cardiovascular and other medical implants. A schematic representation of the multi-layered platform of the PCL, PLGA1, PLGA2 thin films in the specific order to release drugs at different time intervals in accordance with their degradation rates. The same or different drugs can be incorporated into the different BP layers for a steady drug release and avoidance of an excessive burst effect. For instance, in the case of stents, towards the blood, various anti-platelet drugs to avoid thrombosis can be loaded onto the outer—for a short-term effect—or intermediate layers—for short-term and especially medium term effects—, whereas a wide spectrum of anti-inflammatory, antioxidant, and anti-proliferative drugs to reduce inflammation, to inhibit smooth muscle proliferation and arterial restenosis can be loaded to the inner or intermediate layer for a directional drug release towards the atherosclerotic plaque and arterial wall [16-19].

Specifically, the PCL due to its slow degradation rate constitutes the inner layer of the platform, whereas two types of PLGA form its outer and medium layer (PLGA2 and PLGA1). PLGAs with different lactide:glycolide ratios, involving but not limited to PLGAs with lactide:glycolide ratios of 65:35 (PLGA2) and 75:25 (PLGA1) can be used as the outer and intermediate layers respectively, as the higher the content of glycolide units, the lower the time required for degradation. Thus, the quick degradation of PLGA2 enables the quicker drug release from the nanoporous surface for a desirable effectiveness of the implant at the diseased site. In general, the selection of the BP nanolayers to form the nanoplatform in accordance with their degradation rates combined with their optimized nanoporosity, thickness and physicochemical properties are significant parameters that determine the controllable and sustainable drug release from implant or device.

It is to be noted that such design of a drug eluting nanoplatform that can release its payloads in a controlled manner may be utilized to treat various diseases.

Figure 4:
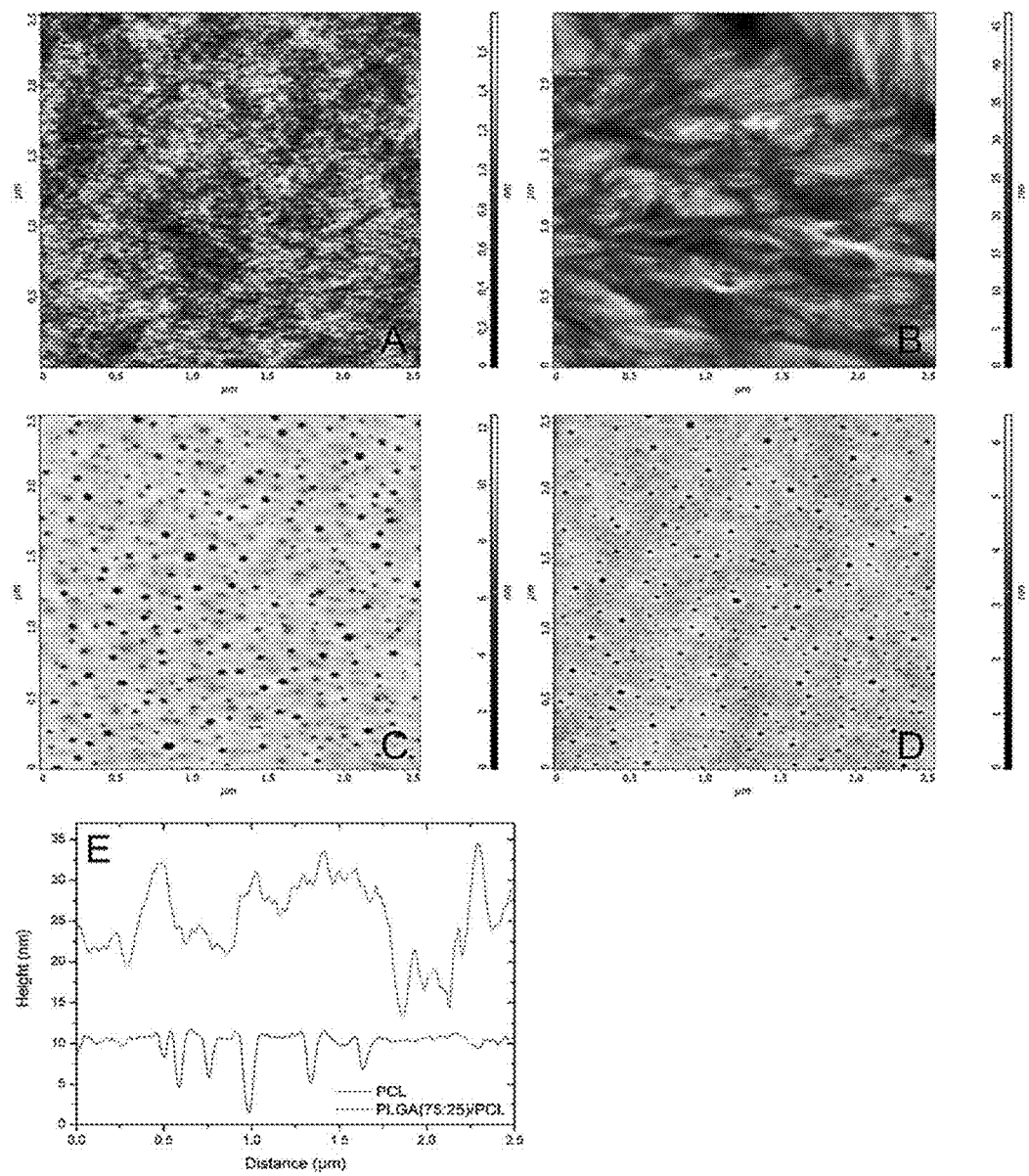
FIG. 4 shows topography images of PLGA single nanolayer (A), PCL single nanolayer B, Dual nanolayer (PLGA1-PCL) C, Triple nanolayer (PLGA2-PLGA1-PCL) D, wherein E shows corresponding X-cross-sections of B and C that reveal the dimensions of the holes between the spherulites of PCL single layers and the pore sizes of PLGA1/PCL dual layers respectively. The results were obtained through Atomic Force Microscopy. PLGA1 refers to PLGA 75:25, and PLGA2 to PLGA 65:35.

FIG. 4 shows the AFM measurements of the single, dual and triple BP nanolayers used for the manufacturing of the drug delivery nanoplatform. Especially, the topography images of PLGA single layer A, PCL single layer B, Dual layer (PLGA1-PCL) C, Triple layer (PLGA2-PLGA1-PCL) D are depicted, wherein E shows corresponding X-cross-sections of B and C that reveal the dimensions of the holes between the spherulites of PCL single layers and the pore sizes of PLGA1/PCL dual layers respectively, wherein PLGA1 refers to PLGA 75:25, and PLGA2 to PLGA 65:35.

The formation of the nanopores observed in the dual and triple BP nanolayers is mainly attributed to spinodal decomposition mechanism due to the polymer phase separation. The selection of the BPs in line with their specific order of deposition should be based on BPs molecular weight, surface free energy, crystallinity, degradation rates, morphology, and properties of the substrate, but not limited thereto. For example, PCL the semi-crystalline and hydrophobic polymer, characterized by spherulites, is deposited onto the substrate and the successive order of deposition of lower crystalline and less hydrophobic polymers such as PLGA is desirable for nanopores formation.

The realization of the AFM measurements is applied for the study of the materials' nanotopography and surface roughness that are related to deposition parameters.

All the materials presented in FIG. 4, were spin-coated at 3000 rpm for 30 sec. The AFM images revealed that the PLGA films were atomically smooth, whereas the PCL films shown in FIG. 4B were less smooth with a surface roughness of ca. 5.5 nm. The surface topography of PCL demonstrated the formation of spherulites with various sizes ranging from 5 to 40 nm, whereas the formation of nanopores was evident in the dual layer polymeric films. Characterization of the pores revealed variation in diameter ranging from 20 to 170 nm and in depth ranging from 2 to 17 nm. The pore density was estimated between 40 and 70 pores/μm2 under different experimental conditions. In the case of the triple layers (PLGA2-PLGA1-PCL), the AFM topography image in FIG. 4D shows high nanoporosity of the thin films. The AFM data demonstrated the formation of nanopores with smaller diameter ranging from 20-150 nm and depth ranging from 1 to 7 nm, compared to the pores formed onto the surface of dual layer polymeric matrices. The pore density of these triple layers was estimated between 2-80 pores/μm2. In FIG. 4E, the corresponding X-cross-sections of FIGS. 4B & C indicate that the holes between the spherulites of PCL single layers reaches ca. 8 nm and the pore depth in the dual layers is ca. 10 min. PLGA1 refers to PLGA 75:25, and PLGA2 to PLGA 65:35.

Thus, the spin coating technique enables the synthesis of the BP thin films characterized by high nanoporosity and uniformity of the nanopores essential for drug delivery. The pore distribution in the nanoporous biomaterials is a key factor for determination of drug release kinetics and its directional control. The tailoring of the nanopores features can be achieved by alteration in deposition parameters. An example of the influence of different experimental conditions onto the nanoporosity (dimensions, volume density, interconnectivity) of the BP thin films for controlled surface properties and subsequent drug loading and release is given in FIG. 5.

Figure 5:
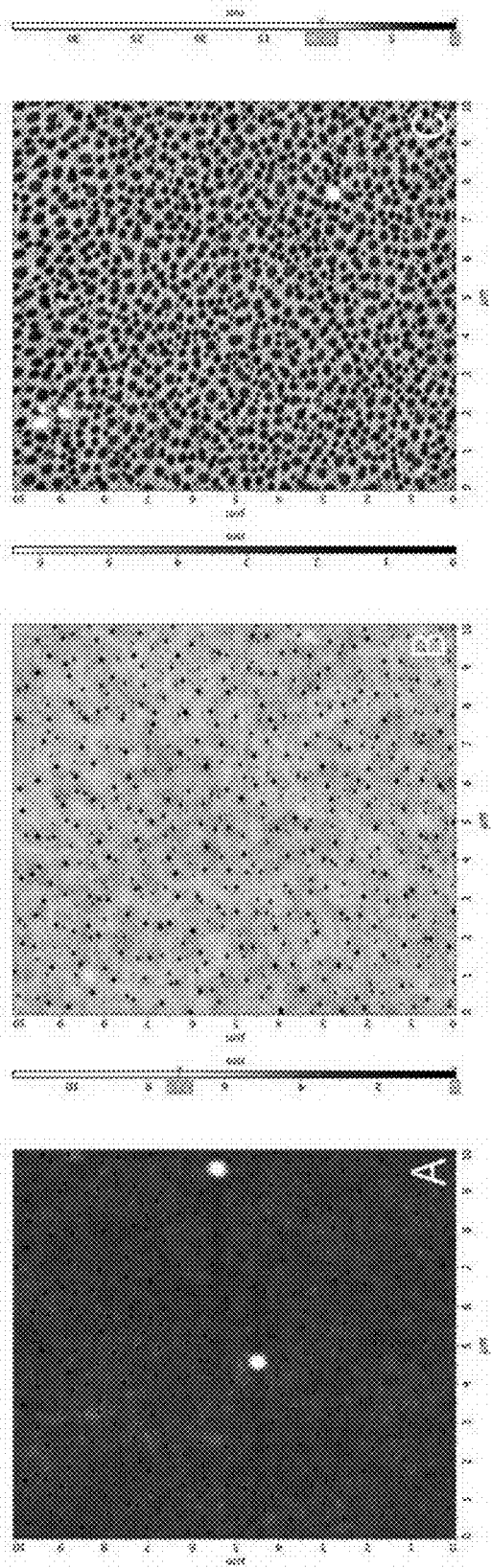
FIG. 5 shows topography images of the triple nanolayer PLGA2-PLGA1-PCL fabricated under variable experimental conditions.

FIG. 5 shows AFM topography images of the triple layer [PLGA2-PLGA1-PCL] fabricated under variable experimental conditions:

(A) polymer concentration of 10 mg ml$^{-1}$, spin-coated at 2000 rpm for 30 sec, (B) polymer concentration of 10 mg ml$^{-1}$, spin-coated at 3000 rpm for 30 sec and (C) polymer concentration of 5 mg ml$^{-1}$, spin-coated at 2000 rpm for 30 sec.

The AFM images demonstrated that by varying the spinning speed and the polymer concentration, multi sized and controllable nanopores can be produced. The increase in the spinning speed leads to an increase in the pore diameter, surface roughness and a decrease in the pore density. The decrease in the polymer concentration of the outer layer of PLGA2 keeping constant the rotation speed and spinning time, results in an increase in pore diameter, pore density and surface roughness of the biomaterials. Thus, the spin coating technique allows the manufacturing of controlled nanoporous BP thin films with reproducible results in the aspect of nanopores with tailored characteristics for optimized drug delivery and release.

Also, the technique allows the manufacturing of nanoporous single layers composed of blends of biodegradable polymers. The formation of nanopores is attributed to the spinodal decomposition mechanism [20].

FIG. 6 shows topography images of the blend single layer (PLGA-PCL) fabricated under variable PCL:PLGA ratios. (A) PCL: PLGA (90:10), (B) PCL:PLGA (50:50) (C) PCL: PLGA (50:50), spin-coated at 2000 rpm for 30 sec. The results were obtained through Atomic Force Microscopy and the scan size was 10 μm×10 μm. (D) PCL:PLGA (10:90) fabricated by gravure printing method with printing speed 10 m/min. (E) corresponding arbitrary-cross-section reveals the dimensions of the nanopores formed in the thin films.

The morphology evolution is strongly dependent on the polymer blend ratio, the surface free energy of the blend polymers and the film thickness. If the weight content of one component in a polymer blend (where the polymers exhibit different surface free energy) is much higher (about 90%) than the other component, then small holes are observed. When this fraction decreases to about 50%, the diameter of the holes increases and the holes starts to coalesce. An analogous behavior is observed in our case comparing FIGS. 6A-C.

In FIG. 6A, where the blend ratio of PCL: PLGA is 90:10, the presence of spherulites is evident whereas in the ratio PCL:PLGA of 50:50 the holes between the spherulites coalesce (FIG. 6B). When the blend ratio of PCL:PLGA ranges from 25:75 up to 5:95, highly nanoporous thin films can be synthesized by spin coating due to the spinodal decomposition mechanism. In FIG. 6C, an example of a nanoporous thin film made of PCL:PLGA 10:90 is presented as developed by spin coating. Another example of a highly nanoporous thin film composed of the polymer blend PCL:PLGA (20:80), as manufactured by spin coating, is depicted in FIG. 6F.

This spinodal decomposition mechanism enables the manufacturing of nanoporous thin films made of BP blends by other wetting, printing and deposition techniques, such as spraying, dipping, gravure printing etc. In FIG. 6D, an example of a nanoporous thin film made of PCL: PLGA 10:90 is fabricated by gravure printing method at the follow steps:

a) The BP PLGA and PCL were mixed at a ratio of 90:10 (PLGA:PCL), in chloroform solvent and total concentration of 10 mg/ml.

b) The polymeric mixture was printed by the gravure printing technique using a printing pattern with cell density of 150 line/inch and cell depth of 4 μm. The deposition was performed onto PET (poly(ethylene terephthalate) substrates.

c) The polymeric solution was printed at a printing range of 2-20 m/min with the optimum at 10 m/min. Then the samples were left to slow dry for 24 h.

The uniformity of the nanopores on the BP nanolayer is obvious wherein variations in the nanopore dimensions enable multiple drug delivery capabilities. An arbitrary cross section of a nanopore in FIG. 6E reveals its accurate dimensions (20-30 nm in diameter and 18 nm in depth). Thus, as a final product single BP layers with tailored nanopores can be developed. These polymer blend thin films (as single layers) can be used as drug delivery nanocoatings for a wide range of implants. An example is presented in FIG. 6G, where the nanoporous PCL:PLGA (10:90) thin film can be loaded with dexamethasone (DEX), at polymer blend:DEX ratio 3:1. Such nanoporous DEX-loaded single nanolayers can be applied for implants where there is a need for reduction of inflammation at the diseased site. A paradigm is their application for intraocular lenses placed after cataract surgery to release anti-inflammatory drugs in a controllable manner. Other benefits of this drug delivery nanosystem for the specific application are the transparency of the samples and their nanometer dimensions that don't affect the vision.

FIGS. 7a and b shows the experimental pseudodielectric functions $<\varepsilon(\omega)>$ (symbols) of the triple PLGA 65:35/PLGA 75:25/PCL/c-Si and PLGA with drug/PLGA/PCL/c-Si films respectively. Moreover, the the solid lines corresponds the simulated ones determined by the use of best-fit results.

The realization of the measurements was performed by Specroscopic Ellipsometry (SE) in the spectral region of Vis-FUV (1.5-6.5 eV). The realization of the measurements in the spectral region of Vis-FUV is applied for the study of the material's optical properties, thickness and optical characteristics either in the form of single or multilayer structure.

The parameterization and analysis of the measured pseudo-dielectric function $<\varepsilon(\omega)>=<\varepsilon1(\omega)>+i<\varepsilon2(\omega)>$ are performed with the use of a geometrical model consisted of air/polymeric thin films/substrate in which the determination of the optical properties of each phase has been realized with the modified Tauc-Lorentz (TL) model [21-24].

In the TL model, the imaginary part ε2(ω) of the dielectric function is determined by multiplying the Tauc density of states with the ε2 that results from the Lorentz oscillator model. Therefore, said TL model provides the capability of determining the fundamental optical gap Eg of the interband transitions, the energy E0, the broadening C and the strength A of each oscillator. The $E_0$ of this model is correlated to the known Penn gap, the energy position where the strong electronic absorption of the material takes place. The imaginary part $\varepsilon_2(\omega)$ of the TL oscillator is given by the following relations: [1,8]

$$\varepsilon_2(\omega) = \frac{AE_0C(E-E_g)^2}{(E^2-E_0^2)^2 + C^2E^2} \cdot \frac{1}{E}, \quad (1)$$
$$E > E_g$$

$$\varepsilon_2(\omega) = 0, \quad (2)$$
$$E \leq E_g,$$

and the real part $\varepsilon_1(\omega)$ is determined by Kramers-Kronig integration, by the relation:

$$\varepsilon_1(\omega) = \varepsilon_\infty + \frac{2}{\pi} P \int_{E_g}^{\infty} \frac{\xi \varepsilon_2(\xi)}{\xi^2 - E^2} d\xi. \quad (3)$$

The fitting parameters in this model are the fundamental band gap energy $E_g$, the amplitude A of the oscillator, the Lorentz resonant energy $E_0$ and its broadening term C The real part of the refractive index (n) and the extinction coefficient (k) f the complex refractive index are related to the dielectric function by [16]:

$$\varepsilon_1 = n^2 - k^2 \quad (4)$$

$$\varepsilon_2 = 2nk. \quad (5)$$

The results show that SE was successfully employed for the determination of the optical properties, thickness and structural characteristics of the spin coated triple polymeric thin films with or without drug. In more detail the $<\varepsilon(\omega)>$ accounts the effect of film thickness and the substrate in addition to the dielectric response of the bulk film, and this is evident by the multiple reflections appear in the spectra. The multiplex reflections are expected to be eliminated when the penetration depth of light becomes smaller than the film thickness. However, the whole spectra are dominated by multiple reflections, since the PLGA and PCL start to absorb at energies above the upper experimental energy limit. By fitting procedure, the films' thicknesses, the bulk dielectric functions and the refractive indices of the produced PLGA films with or without drug and PCL films were calculated.

For example, in the case of the triple BP nanoplatform loaded with DPM in the external layer, the thickness of the drug delivery nanolayer was measured to be 134 nm, whereas the medium PLGA2 layer and inner PCL layer exhibit thicknesses of 32 nm and 42 nm respectively. The thicknesses of the thin films can be controlled by alterations in deposition parameters and polymer, drug concentrations.

FIG. 8 shows the refractive index n of the bulk materials of the single layer polymeric films PLGA 75:25 and PCL, the PLGA 75:25 and PCL from the dual layer film, and the PLGA 65:35 and PCL from the triple layer film as calculated from the analysis of the $<\varepsilon(\omega)>$. The formation of nanopores or voids in the dual (PLGA75:25-PCL) and triple layer films (PLGA65:35-PLGA75:25-PCL) was verified by the SE studies. More specifically, from FIG. 8 it is evident the reduction of the n values in both PLGA and PCL films, that consist the dual and triple layer polymeric film, in comparison to those derived for the single layer films. The decrease in its n values may be due to the reduction in the density of a material and partially due to the surface and interface roughness in PCL and PCL/PLGA layers. Moreover, it is noticeable that a more drastic reduction in the n values was deduced for the PCL films comparing to the PLGA. Therefore, we can interpret the SE results with the nanopores formation in the dual and triple layer films.

The data provided by the analysis of the AFM and SE measurements are very crucial, since the monitoring and analysis of the nanoporosity, thickness, structural and optical characteristics of the BP single or multi-layers enable the control and optimization of the drug delivery and release capacities of the nanoplatform. Especially, the optical characterization of the PLGA nanolayers is essential in the application of the drug delivery nanoplatform for intraocular lenses placed after cataract surgery to release anti-inflammatory, antibiotics and other drugs in a controllable manner.

The pharmacotherapy agent that can be loaded into the present nanoporous platform for cardiovascular and other implantable devices includes but it is not limited to the following one or more substance: aspirin, dipyridamole, clopidogrel, heparin, everolimus, paclitaxel, sirolimus, rapamycin, rostacyclin, corticosteroids, methylprednisolone, dexamethazone, tacrolimus, statins, methotraxate, anti-inflammatory drugs and antibiotics, hormones, peptides, angiogenic factors, hirudin, cyclosporine, abciximab, tirofiban, factor Xa inhibitors, eptifibatide, ceftriaxone-sulbactam, genes, growth factors, etc.

FIG. 9a shows an example of the delivery of an antiplatelet drug, the dipyridamole (DPM), within the nanopores of the external layer of the nanoplatform and its drug release kinetics. Especially, the cumulative release profiles of DPM from the outer layer PLGA2 of the multi-layer nanoplatform (PLGA2-PLGA1-PCL) with PLGA2: DPM 3:1 ratio. The results were obtained through UV-visible spectrophotometer measurements of the free drug that absorbs at 292 nm. The release profiles, indicate the burst release stage during the first 5 h (inset to FIG. 9a), an exponential release rate during the first 20 days; approximately constant release rate during days 20-60 and finally followed by an increased release up to days 70. This indicates that the assembled therapeutic multilayer was slowly disassembled with releasing DPM in a controlled manner. The DPM burst effect and release profile during the first 2 stages was typical of diffusion controlled systems. The third and fourth phase of constant release rate presumably involved degradation of the PLGA combined with diffusion of the remaining drug that was more firmly attached to polymer. Herein, PLGA1 is referring to PLGA 75:25, and PLGA2 to PLGA 65:35.

The body of invention entails the usage of different BP polymers either hydrophobic or hydrophilic to form the nanolayers of the platform in accordance with each medical need. Especially, in the case of vascular implants and devices, a hydrophilic external nanolayer, such as Poly(vinyl alcohol (PVA), and Polyethylene glycol (PEG), is desirable for improved biocompatibility. An example of the structure of a multi-layer nanoplatform with [PVA-PLGA2-PLGA1-PCL] loaded with DPM in PLGA2 thin film and the drug release kinetics are presented in FIG. 9b. PLGA1 is referring to PLGA 75:25, and PLGA2 to PLGA 65:35.

There is a PLGA2:DPM 3:1 ratio wherein the inset image presents the AFM topography of the nanoporous platform, and the inset graph depicts the burst effect that occurs during the first 5 hours. The nanopores formation is evident on the PVA external layer, showing the ability of the fabrication method to develop nanopores not only to hydrophobic but also to hydrophilic BPs. The drug release kinetics showed that by the usage of the PVA thin film there is a reduction and more sustained release of the initial concentration of the drug during the first 5 hours, essential for avoidance of any undesirable side effects at the diseased site caused by the drug burst release.

A diversity of drugs can be delivered into the nanolayers of the platform taking into account each medical need. The type of drugs, drug concentration, types of BP polymers affect the drug release kinetics. In the case of implants where there is a need for anti-inflammatory agents, an example of the nanoplatform that delivers corticosteroids is presented in FIG. 9c. This Fig. shows the dexamethasone (DEX) cumulative release profiles from the outer layer PLGA2 (PLGA 65:35) of the multi-layer nanoplatform [PLGA2-PLGA1-PCL] with PLGA2: DEX 3:1 ratio wherein the inset graph depicts the burst effect that occurs during the first 5 hours. Herein, PLGA1 is referring to PLGA 75:25, and PLGA2 to PLGA 65:35.

By varying the polymer:drug ratio in the BP layers, differences in nanopores characteristics of the materials occur, indicative of the multiplexicity of the drug delivery capabilities.

FIG. 10 shows the topography images of the triple nanoplatform (PLGA2-PLGA1-PCL) loaded with DPM at PLGA2:DPM 2:1 ratio as fabricated by spin-coating at 3000 rpm for 30 sec (left image) and after its degradation in PBS solution for 15 min (right image). The results were obtained through AFM and the scan size was 2.5 µm×2.5 µm. PLGA1 is referring to PLGA 75:25, and PLGA2 to PLGA 65:35.

A uniform distribution of the nanopores with variation in size and depth in the drug loaded BP layer at PLGA2:DPM of 2:1 ratio is evident wherein there is an increase in dimensions of the nanopores as compared to the triple BP nanolayers presented in FIG. 5C, where the ratio of PLGA2: DPM is 3:1. This leads to different drug delivery capacities that determine the drug eluting profiles.

FIG. 11 shows the DPM cumulative release profiles from the external nanolayer of the nanoplatform [PLGA2 (PLGA 65:35)-PLGA1 (PLGA 75:25)-PCL] with PLGA2:DPM to be 2:1 ratio, wherein the inset graph depicts the burst effect that occurs during the first 5 hours.

The results were obtained through UV-visible spectrophotometer measurements of the free drug that absorbs at 292 nm.

As compared to the drug release kinetics presented in FIG. 9a, a higher DPM cumulative release is observed due to the higher drug content and to the increase in pore dimensions of the specific sample.

FIG. 12a shows the dipyridamole cumulative release profiles from the medium layer of the nanoplatform [PLGA2 (PLGA 65:35)-PLGA1 (PLGA75:25) with DPM-PCL] with PLGA1:DPM at 2:1 ratio, wherein the inset graph depicts the burst effect that occurs during the first 5 hours. The results were obtained through UV-visible spectrophotometer measurements of the free drug that absorbs at 292 nm. FIG. 12b, shows the dexamethasone (DEX) cumulative release profiles from the medium layer PLGA2 (PLGA 65:35) of the multi-layer nanoplatform [PLGA 2 (PLGA 65:35)-PLGA 1 (PLGA 75:25) with DEX-PCL] with PLGA2:DEX 3:1 ratio wherein the inset graph depicts the burst effect that occurs during the first 5 hours.

As compared to the drug release kinetics presented in FIGS. 9a, 9c, and 11, where the drugs are loaded in the external layer of the nanoplatform, there is a more steady and slow drug release from the medium layer which is desirable for medium and long term therapeutic effects.

FIG. 12c shows the comparative diagram of the cumulative release profiles of the DPM and DEX drugs in relation to their position within the external or medium thin films of the three nanolayer platform [PLGA2-PLGA1-PCL] keeping constant the drug: polymer ratio. PLGA1 refers to PLGA 75:25, and PLGA2 to PLGA 65:35. It can be deduced that the nanoporosity, thickness, biodegradation rate of the BP nanolayers, type of drug, and drug position, controls the drug release kinetics from the nanoplatform. So, in the external BP nanolayer where the degradation rate is higher, therapeutic agents, drugs, peptides, growth factors, for short-term therapeutic activities can be delivered, wherein for medium-term and sustained therapeutic effects the appropriate agents or drugs should be delivered in the medium nanolayer. To achieve long-term therapeutic effects, the drugs, agents should be delivered in the internal BP nanolayer that exhibits slow degradation rates.

In overall, the performance of the drug eluting nanoplatform made from biodegradable polymers can be tuned by tailoring their molecular weight, crystallinity, surface free energy, hydrophilicity, monomers ratio and polymer blend ratio. However, additional factors are of equal importance. These include processing and manufacturing parameters, device design, and the site of implantation.

Nanoporosity is determined mainly, but not limited, by the structural properties of the BPs, polymer concentration and polymer blend ratio, the order of the successive deposition of the BP nanolayers and the biodegradation rate of the BPs.

The nanoporosity, thickness and biodegradation rate of the BP nanolayers controls the drug release kinetics from the nanoplatform. By alterations in deposition parameters such as the polymer:drug ratio, polymer concentration, drug concentration, drug position, etc, desirable drug release profiles for short-term, medium-term and long-term use can be accomplished to meet the demands for various medical implants.

The applications of the device body of the present invention includes but it is not limited to the following ones: biomedical tools, drug eluting medical devices and implants such as vascular and non vascular stent, drug eluting stent, guidewire, balloon cardiac catheter, cardiac pacemaker and implantable defibrillator, cardiac valve, surgical implant material, surgical tool, ocular and lens implant, orthopedic, spine and dental implants, food packaging, clothing, etc.

REFERENCES

[1] "Development of microporous covered stents: geometrical design of the luminal surface" Y. Nakayama, S. Nishi, H. Ishibashi-Ueda, Y. Okamoto, Y. Nemoto Int J Artif Organs. 28 (6), 600-608 (2005).

[2] "Synergy of passive coating and targeted drug delivery: the tacrolimus-eluting Janus CarboStent" A. L. Bartorelli, D. Trabattoni, F. Fabbiocchi, P. Montorsi, S. de Martini, G. Calligaris, G. Teruzzi, S. Galli, P. Ravagnani J Interv Cardiol. 16(6), 499-505 (2003).

[3] "Mechanisms of controlled drug release from drug-eluting stents" G. Acharya, K. Park. Mechanisms of controlled drug release from drug-eluting stents. Adv Drug Deliv Rev. 58, 387-40 (2006)

[4] EP1557183 A1/Cordis Corp (US) (Jul. 27, 2005).

[5] CN101862478 A/Xinhua Hospital affiliated to Shanghai Jiao Tong University School (Oct. 20, 2010).

[6] "Late Thrombosis of Drug-Eluting Stents: A Meta-Analysis of Randomized Clinical Trials" A. Bavry, D. Kumbhani, T. Helton, P. Borek, G. Mood, D. Bhatt. Am J Med. 119, 1056-61 (2006).

[7]. "Late thrombosis after paclitaxel eluting stent implantation" F. Liistro, A. Colombo. Heart. 86, 262-64 (2001).

[8] "Nanomedicine for the reduction of the thrombogenicity of stent coatings" V. Karagkiozaki, S. Logothetidis, S. Kassavetis, G. Giannoglou. Int J Nanomedicine 5, 239-248 (2010).

[9] "Nanomedicine Highlights in Atherosclerosis: A Review" V. Karagkiozaki, J. Nanoparticle Res. 15, 1529-1546 (2013).

[10] "Controlled drug release using nanoporous anodic aluminium oxide on stent" H. Kang, D. J. Kim, S. Park, J. Yoo, Y. S. Ryu Thin Solid Films 515(51), 84-87 (2007).

[11] "Delivery of antiangiogenic and antioxidant drugs of ophthalmic interest through a nanoporous inorganic filter" K. E. Orosz, S. Gupta, M. Hassink, M. Abdel-Rahman, L. Moldovan, F. H. Davidorf. Mol Vis. 10, 555-65 (2004).

[12] "Self-ordering Electrochemistry: A Simple Approach for Engineering Nanopore and Nanotube Arrays for Emerging Applications" D. Losic, L. Velleman, K. Kant, T. Kumeria, K. Gulati, J. G. Shapter, et al. Aust J Chem. 64, 294-301 (2011).

[13] "Advances in top-down and bottom-up surface nano fabrication: techniques, applications and future prospects" A. Biswas, I. S. Bayer, A. S. Biris, T. Wang, E. Dervishi, F. Faupel, Adv. Colloid Interface Sci. 170, 2-27 (2012).

[14] "Composite Block Polymer-Microfabricated Silicon Nanoporous Membrane" E. E. Nuxoll, M. A. Hillmyer, R. Wang, C. Leighton, R. A. Siegel ACS Appl Mater Interfaces. 1, 888-93 (2009).

[15] "Scanning electron microscopic analysis of different drug eluting stents after failed implantation: from nearly undamaged to major damaged polymers" M Wiemer, T Butz, W Schmidt, K P Schmitz, D Horstkotte, C Langer Catheter Cardiovasc Interv. 75(6), 905-11 (2010).

[16] "Drug-eluting stents: the next generation" J A Shand, I B A Menown Interventional Cardiology 2(3), 341-350 (2010).

[17] "Role of stent design and coatings on restenosis and thrombosis" H Hara, M Nakamura, J C Palmaz, R S Schwartz Adv Drug Deliv Rev. 58(3), 377-86 (2006).

[18] "Coronary Stents: Current Status" S Garg, P Serruys J Am Coll Cardiol.; 56, 1-42 (2010).

[19] "Tacrolimus-eluting carbon-coated stents versus sirolimus-eluting stents for prevention of symptom-driven clinical end points" J M Siller-Matula, I Tentzeris, B Vogel, S Schacherl, R Jarai, A Geppert, G Unger, K Huber Clin Res Cardiol. 99(10), 645-50 (2010).

[20] "Surface Topography and Composition of Deuterated Polystyrene-Poly (bromostyrene) Blends" S Affrossman, G Henn, S O'Neill, P Pethrick, M Stamm Macromolecules 29, 5010-5016 (1996).
[21] "THIN FILMS HANDBOOK: Processing, Characterization and Properties" in "In-situ monitoring in thin films during growth with spectroscopic ellipsometry" S. Logothetidis, ed. by Hari Singh Nalwa (Academic Press, 2001).
[22] U.S. Pat. No. 7,777,882, "Method for the in-situ and real-time determination of the thickness, optical properties and quality of transparent coatings during their growth onto polymeric substrates and determination of the modification, activation and the modification depth of polymeric materials surfaces" Logothetidis Stergios
[23] "HANDBOOK OF NANOPHYSICS: Principles and Methods" in "Nanometrology" S. Logothetidis, ed. by Klaus D. Sattler (CRF Press, 2011).
[24] "Parameterization of the optical functions of amorphous materials in the interband region" G. E. Jellison, and F. A. Modine Appl. Phys. Lett. 69, 371 (1996).

The invention claimed is:

1. A method for the fabrication of biodegradable polymeric thin films comprising the following preparation steps:
    (a) selecting biodegradable polymers (BP) based on their degradation rates, monomers ratio, molecular weight, concentration and a polymer blend ratio;
    (b) spin coating the selected polymers onto cleaned inorganic or organic substrates and forming multi-layers;
    (c) preforming multi-dimensional nanopores with tailored characteristics in all of the multi-layers before administering;
    (d) providing a payload in one or more of the multi-layers and forming a delivery nanoplatform for controlled and steady release of the payload contained therein;
    (e) preparing a BP solution from said biodegradable polymers which is spin coated on the nanoplatform and then dried;
    (f) spin coating the payload comprising an organic solution containing an active drug and BP at a ratio that provides a desired active drug concentration, well dissolved in organic solvent onto the said biodegradable polymeric layers and sterilizing; wherein said steps are carried out in the specified order; and
    (g) providing the payload in at least one each of inner and outer layers of the multi-layers wherein the outer layer has a higher degradation rate than the inner layer.

2. The method according to claim 1, wherein the tailored characteristics includes characteristics of film nanopores, surface nanotopography and roughness of said polymeric thin films determined by atomic force microscopy and wherein the thickness, drug concentration and distribution, optical properties, and quality of the films is calculated by using Spectroscopic Ellipsometry.

3. The method according to claim 1, wherein during said steps (a) and (f), a drug loaded biodegradable polymer or polymer blend is selected to be deposited in a way that the BP with slow degradation rate constitutes the inner layer of the platform for a prolonged drug release whereas the outer and intermediate drug loaded layers have quicker degradation rates for short and medium term drug release.

4. The method according to claim 1, wherein the BP is a blend of biodegradable polymers.

5. The method according to claim 1, wherein said thin films possess uniformly distributed nanopores with tailored characteristics.

6. The method according to claim 4, further comprising synthesizing with a gravure printing technique nanoporous thin films made of blends of biodegradable polymers and the preparation steps consist of: a) selecting biodegradable polymers (BP) based on their degradation rates, monomers ratio, molecular weight, b) preparing a polymer blend by dissolving the said BPs at specific ratio in organic solvent, c) printing the polymeric mixture by a gravure printing technique under selected printing parameters and d) leaving the samples to dry.

7. The method according to claim 1, wherein the payload is a therapeutic agent selected from the group consisting of the following substances: drugs, genes, peptides, nanomedicines, compounds, and mixtures of any of them.

8. The method according to claim 1, wherein the nanoporous platform comprises biodegradable polymeric thin films as multi layers or as blends and is formed into a medical implant or device selected from the group consisting of a vascular stent, a non-vascular stent, a drug eluting stent, a guidewire, a balloon cardiac catheter, a cardiac pacemaker, an implantable defibrillator, a cardiac valve, a surgical implant material, a surgical tool, an ocular lens implant, an orthopedic implant, a spine implant and a dental implant.

9. The method according to claim 1, wherein the BP is a polymer blend of PCL:PLGA in a proportion ranging from 25:75 to 5:95.

10. The biodegradable polymeric thin films produced according to the method of claim 1, that comprise nanopores with tailored characteristics in the form of multi nanoporous layers and blend single nanoporous layers.

11. The biodegradable polymeric thin films according to claim 10, that are highly nanoporous, loaded with different drugs, comprising multi layers and providing controlled delivery and release of the drugs.

12. The biodegradable polymeric thin films according to claim 10, wherein the biodegradable polymers that form a delivery nanoplatform are deposited in a way that the BP with a slow degradation rate constitutes an inner layer of the nanoplatform for a prolonged drug release whereas the outer and intermediate layers have quicker degradation rates for short and medium term drug release.

13. A method for the fabrication of biodegradable polymeric thin films comprising the following preparation steps:
    (a) selecting biodegradable polymers (BP) based on their degradation rates, monomers ratio, molecular weight, concentration and a polymer blend ratio;
    (b) spin coating the selected polymers onto cleaned inorganic or organic substrates; preforming multi-dimensional nanopores with tailored characteristics in all of multi-layers or single layer blends before administering, providing a payload in the multi-layers or single layer, forming a delivery nanoplatform that achieves a controlled and steady release of the payload contained therein;
    (c) preparing the payload comprising a BP solution from said biodegradable polymers which is spin coated on the nanoplatform and then left to dry; and
    (d) providing the payload in at least one each of inner and outer layers of the multi-layers wherein the at least one outer layer has a higher degradation rate than the at least one inner layer.

* * * * *